(12) United States Patent
Nakagawa et al.

(10) Patent No.: US 11,969,235 B2
(45) Date of Patent: Apr. 30, 2024

(54) SENSOR MODULE, METHOD FOR MANUFACTURING SENSOR MODULE, AND BLOOD PRESSURE MEASUREMENT DEVICE

(71) Applicant: OMRON HEALTHCARE Co., Ltd., Kyoto (JP)

(72) Inventors: Yuki Nakagawa, Kyoto (JP); Tsuyoshi Hamaguchi, Kyoto (JP); Takashi Fuchimoto, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 809 days.

(21) Appl. No.: 16/950,333

(22) Filed: Nov. 17, 2020

(65) Prior Publication Data
US 2021/0068684 A1    Mar. 11, 2021

Related U.S. Application Data

(63) Continuation of application No. PCT/JP2019/020044, filed on May 21, 2019.

(30) Foreign Application Priority Data

May 24, 2018   (JP) .................................. 2018-099721

(51) Int. Cl.
*A61B 5/022*    (2006.01)
*A61B 5/021*    (2006.01)

(52) U.S. Cl.
CPC ...... *A61B 5/02233* (2013.01); *A61B 5/02108* (2013.01); *A61B 2562/0247* (2013.01); *A61B 2562/12* (2013.01); *Y10T 29/49007* (2015.01)

(58) Field of Classification Search
CPC ................ A61B 5/681; A61B 5/02233; A61B 2562/0247; A61B 5/024; A61B 5/021; Y10T 29/49007

(Continued)

(56) References Cited

U.S. PATENT DOCUMENTS

| 6,918,879 B2* | 7/2005 | Ting ....................... A61B 5/021 600/503 |
| 7,674,231 B2* | 3/2010 | McCombie ........ A61B 5/02125 600/481 |

(Continued)

FOREIGN PATENT DOCUMENTS

| CN | 105990515 A | 10/2016 |
| JP | 111378/1980 | 2/1982 |

(Continued)

OTHER PUBLICATIONS

International Preliminary Report on Patentability dated Nov. 26, 2020 in International (PCT) Application No. PCT/JP2019/020044.

*Primary Examiner* — Thiem D Phan
(74) *Attorney, Agent, or Firm* — Wenderoth, Lind & Ponack, L.L.P.

(57) ABSTRACT

Provided is a sensor module, a method for manufacturing a sensor module, and a blood pressure measurement device that can improve the holding force onto a soft portion. A sensor module 63 of a blood pressure measurement device 1 includes: a sensor base 72; a pressure sensor portion 71 fixed to the sensor base 72; a sensor head cover 73 including, on an outer surface, an opening 73a in a region that comes into contact with a wrist 100 and an inner surface 73g formed with unevenness, the sensor head cover 73 being fixed to the sensor base 72 and forming a gap portion 79 that communicates with the opening 73a between the inner surface 73g, the sensor base 72, and the pressure sensor portion 71; and
a soft portion 74 disposed in the gap portion 79 and, at least, filling up the opening 73a and covering the pressure sensor portion 71.

8 Claims, 25 Drawing Sheets

(58) Field of Classification Search
USPC .................................. 29/595, 428, 593, 846
See application file for complete search history.

(56) References Cited

U.S. PATENT DOCUMENTS

2015/0173639 A1  6/2015  Ichida et al.
2016/0093792 A1  3/2016  Xiong et al.

FOREIGN PATENT DOCUMENTS

| JP | H01288228 A | 11/1989 |
| JP | 6-14894 A | 1/1994 |
| JP | 2006-239114 A | 9/2006 |
| JP | 2010-233883 A | 10/2010 |
| JP | 2011-200267 A | 10/2011 |
| JP | 2016-72589 A | 5/2016 |
| WO | WO 2014/007307 A1 | 1/2014 |
| WO | WO 2017/170838 A1 | 10/2017 |

* cited by examiner

[FIG. 1]
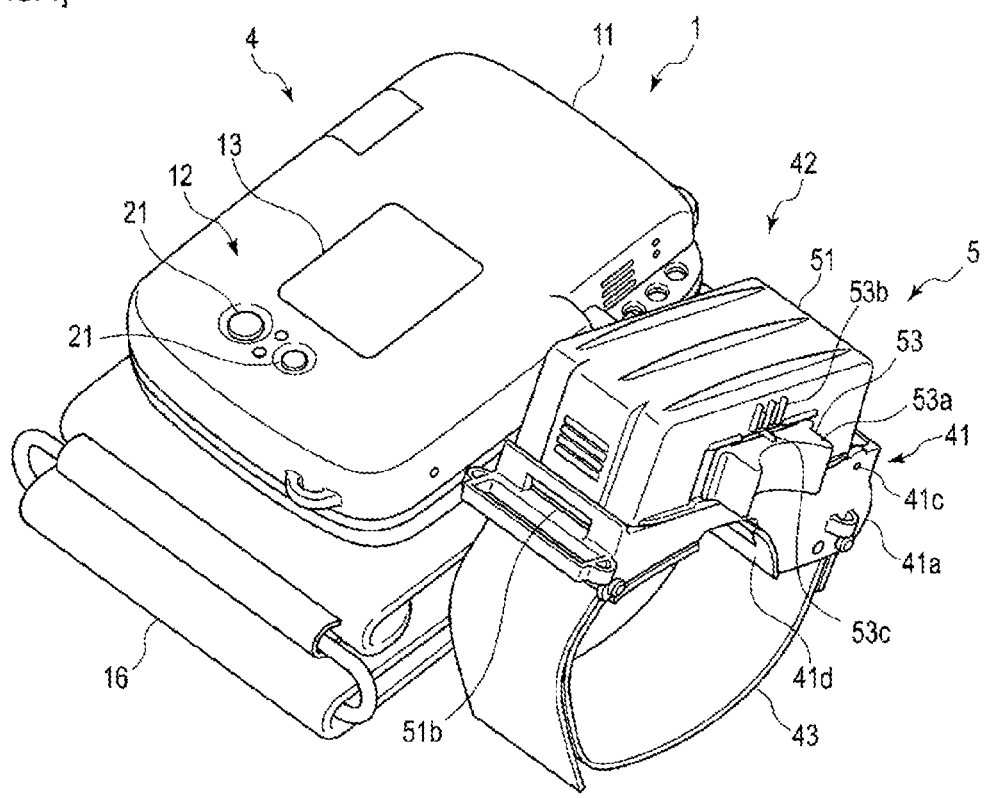

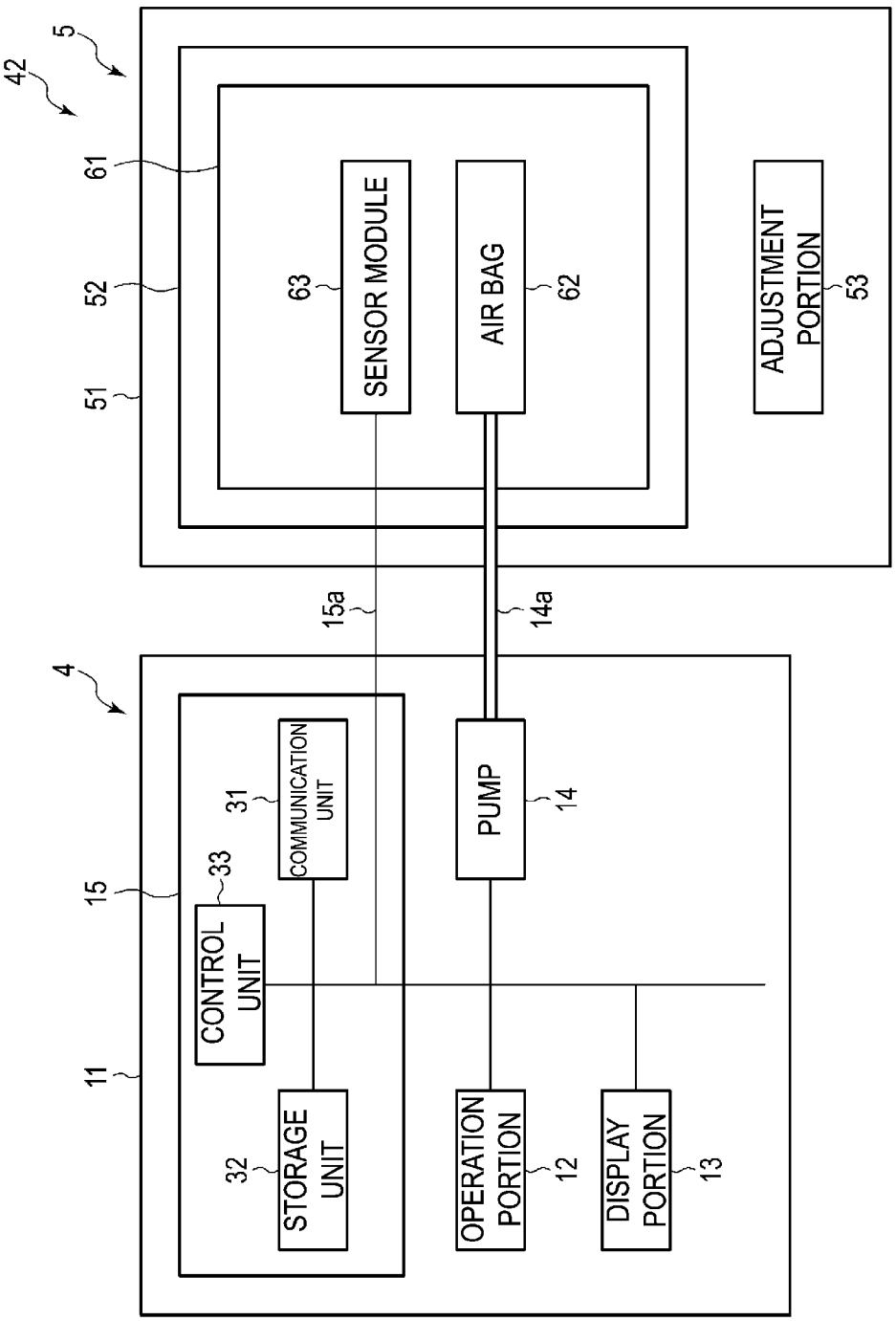

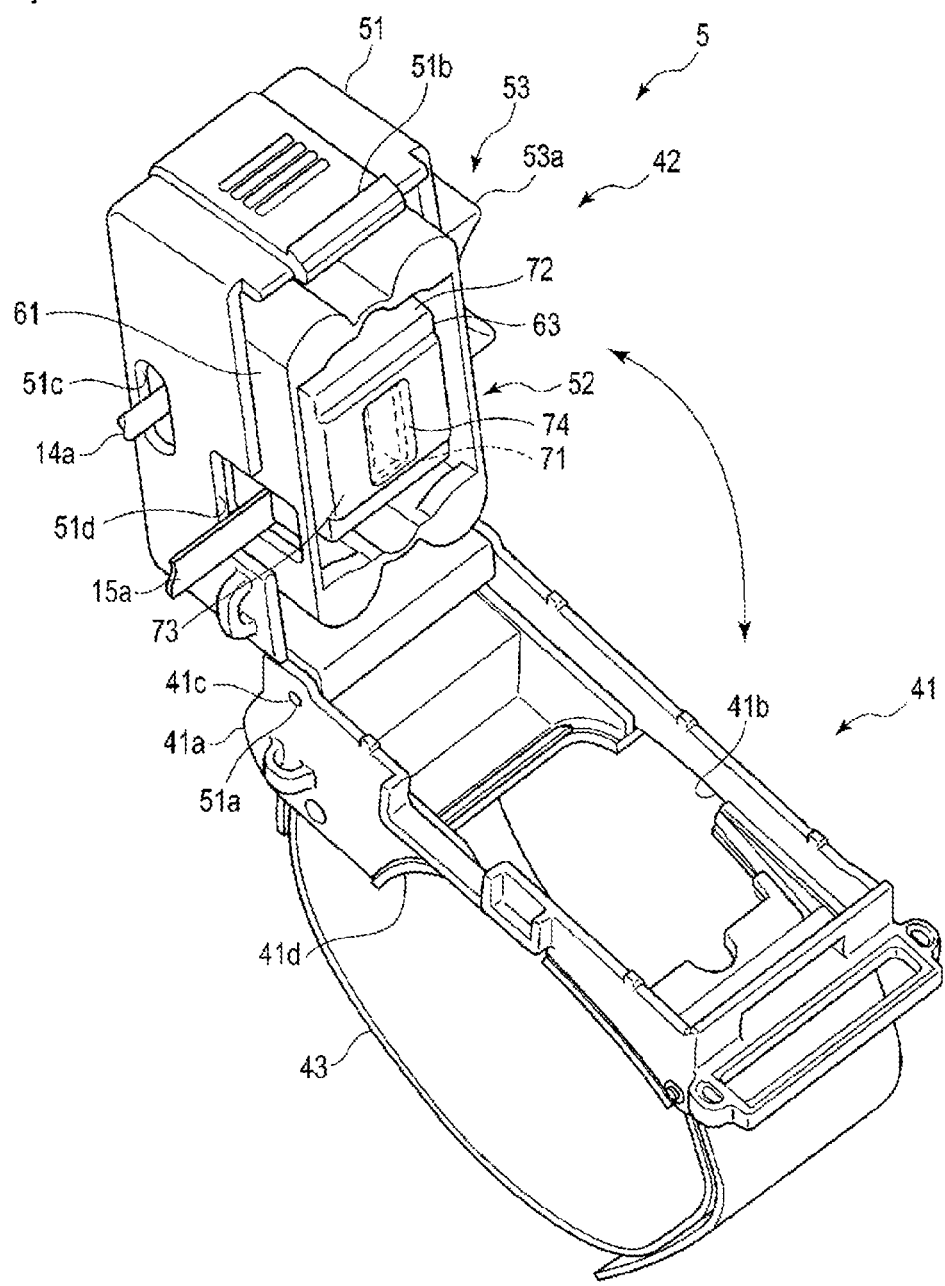
[FIG. 3]

[FIG. 4]
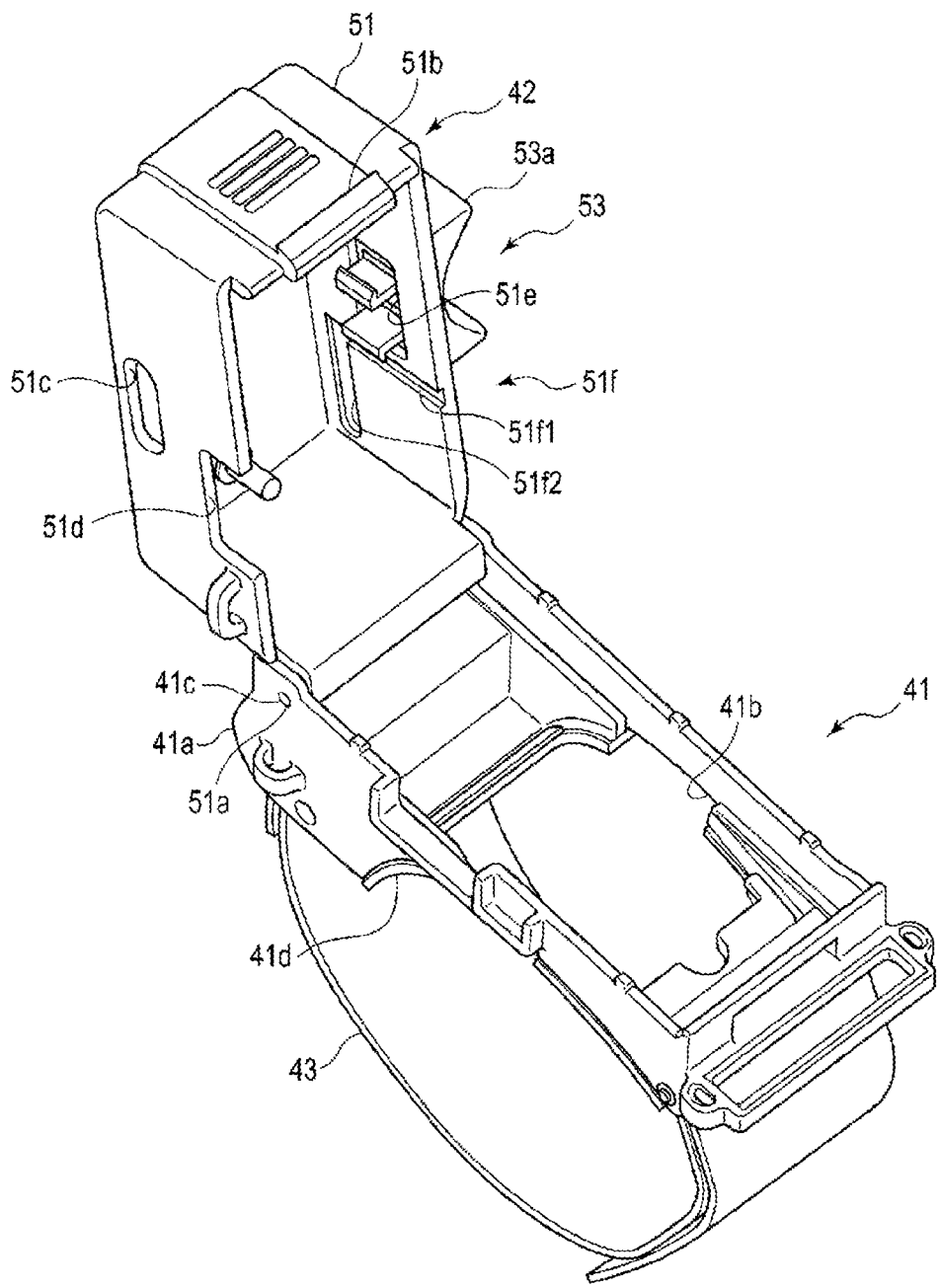

[FIG. 5]
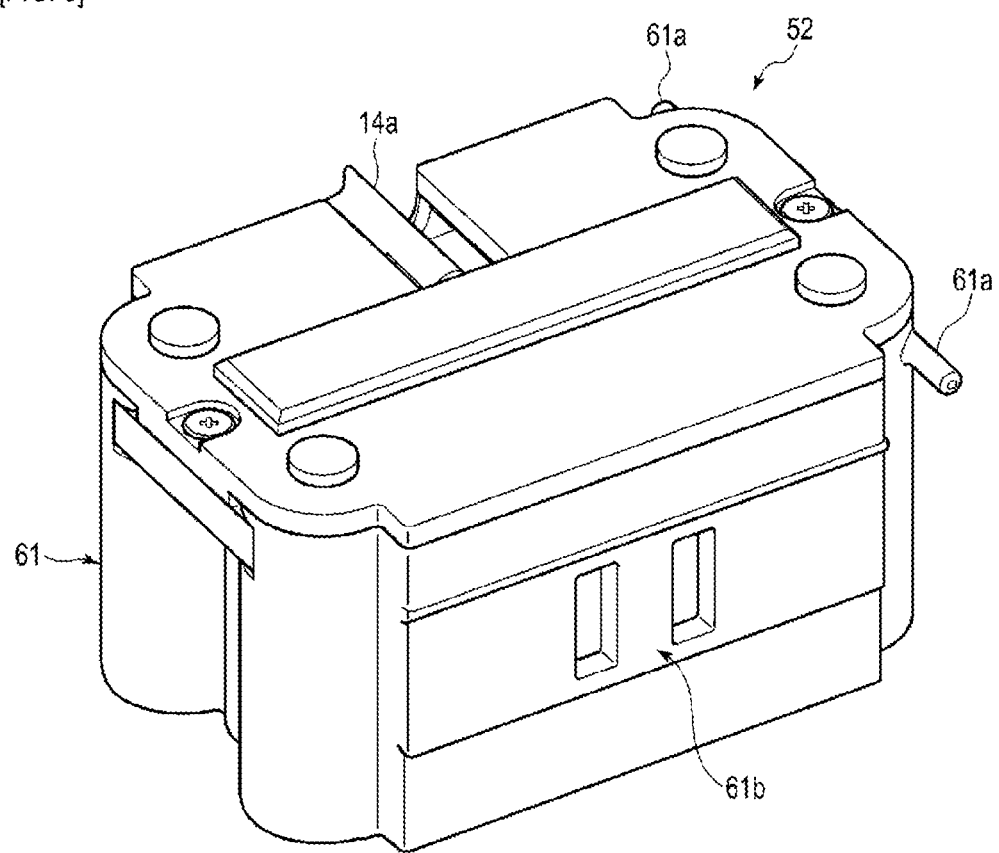

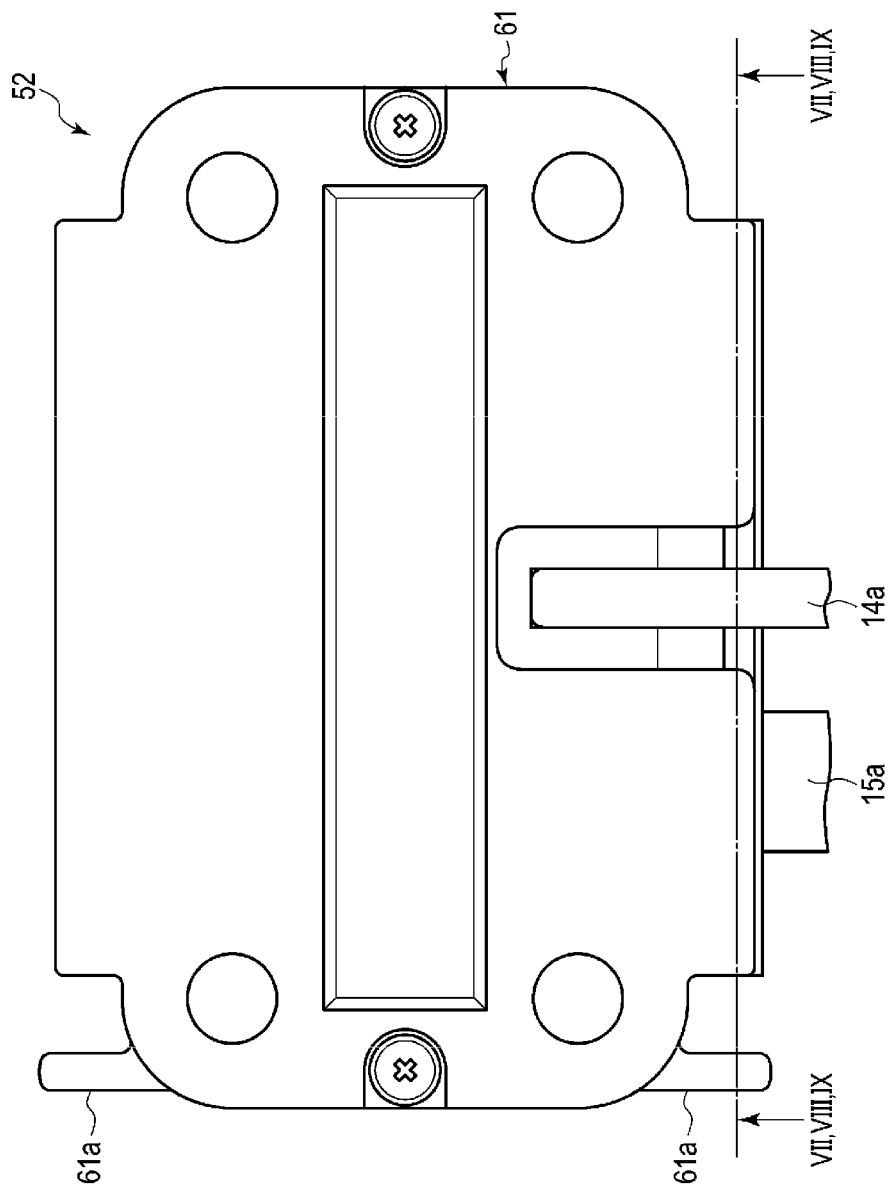
[FIG. 6]

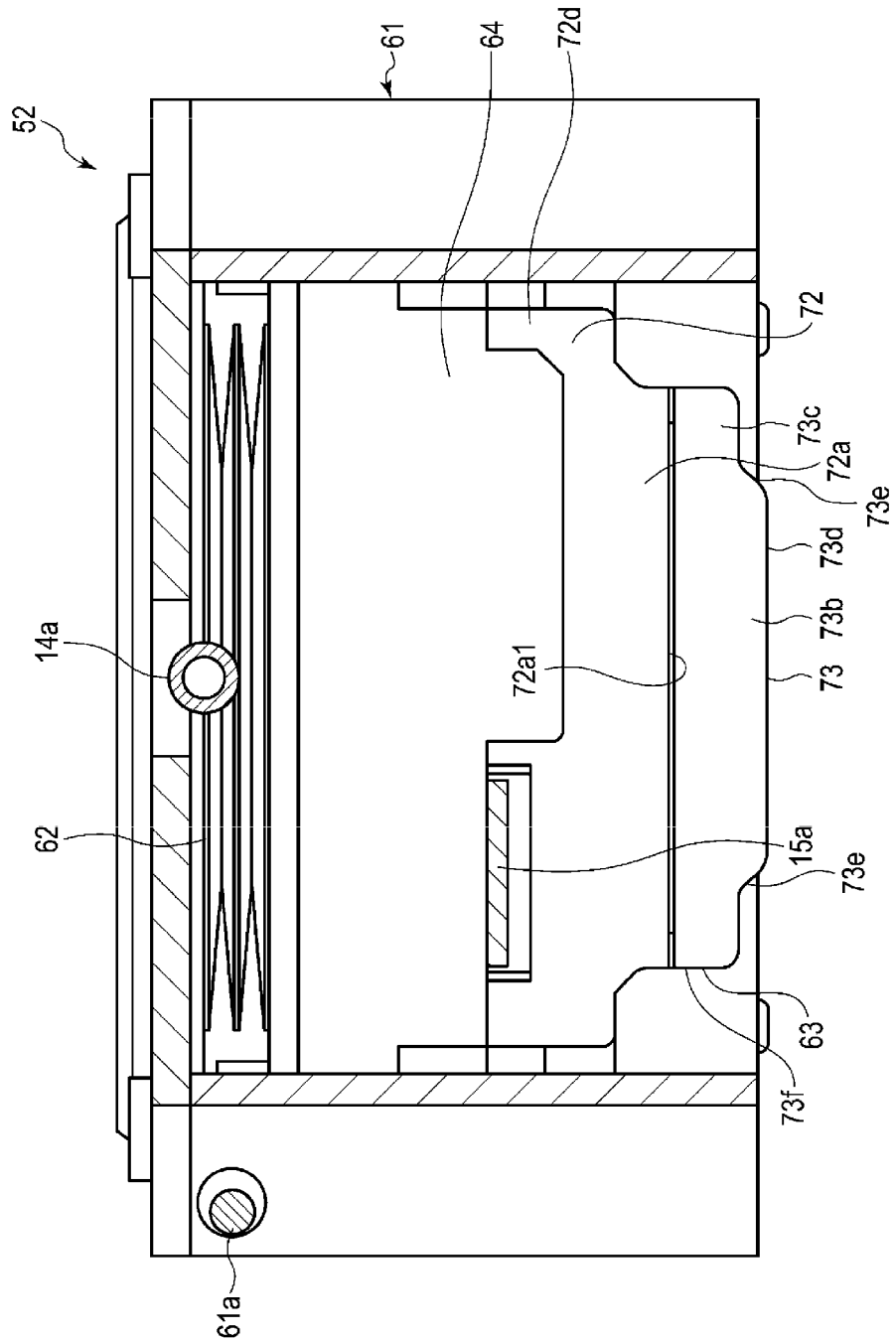

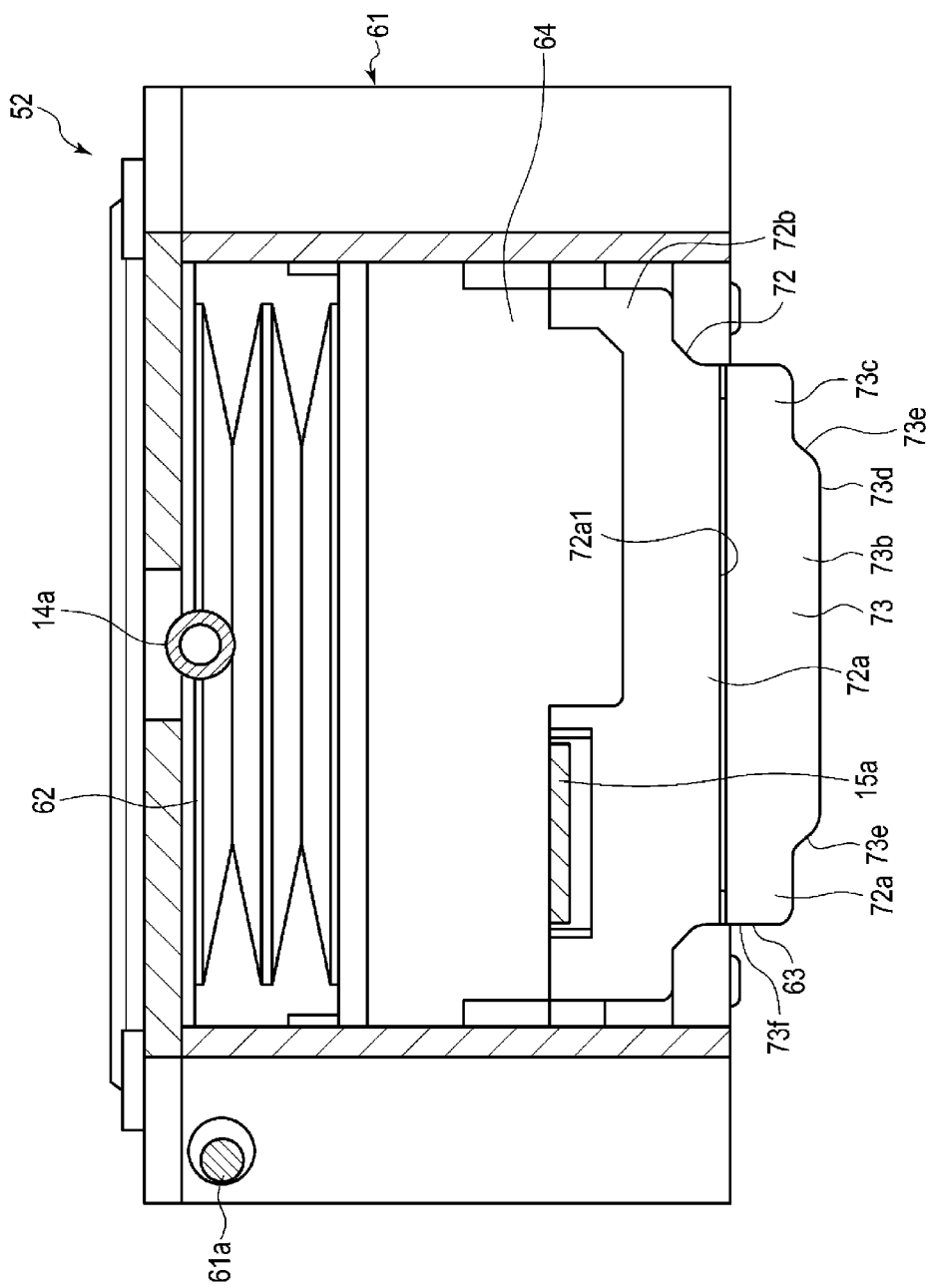

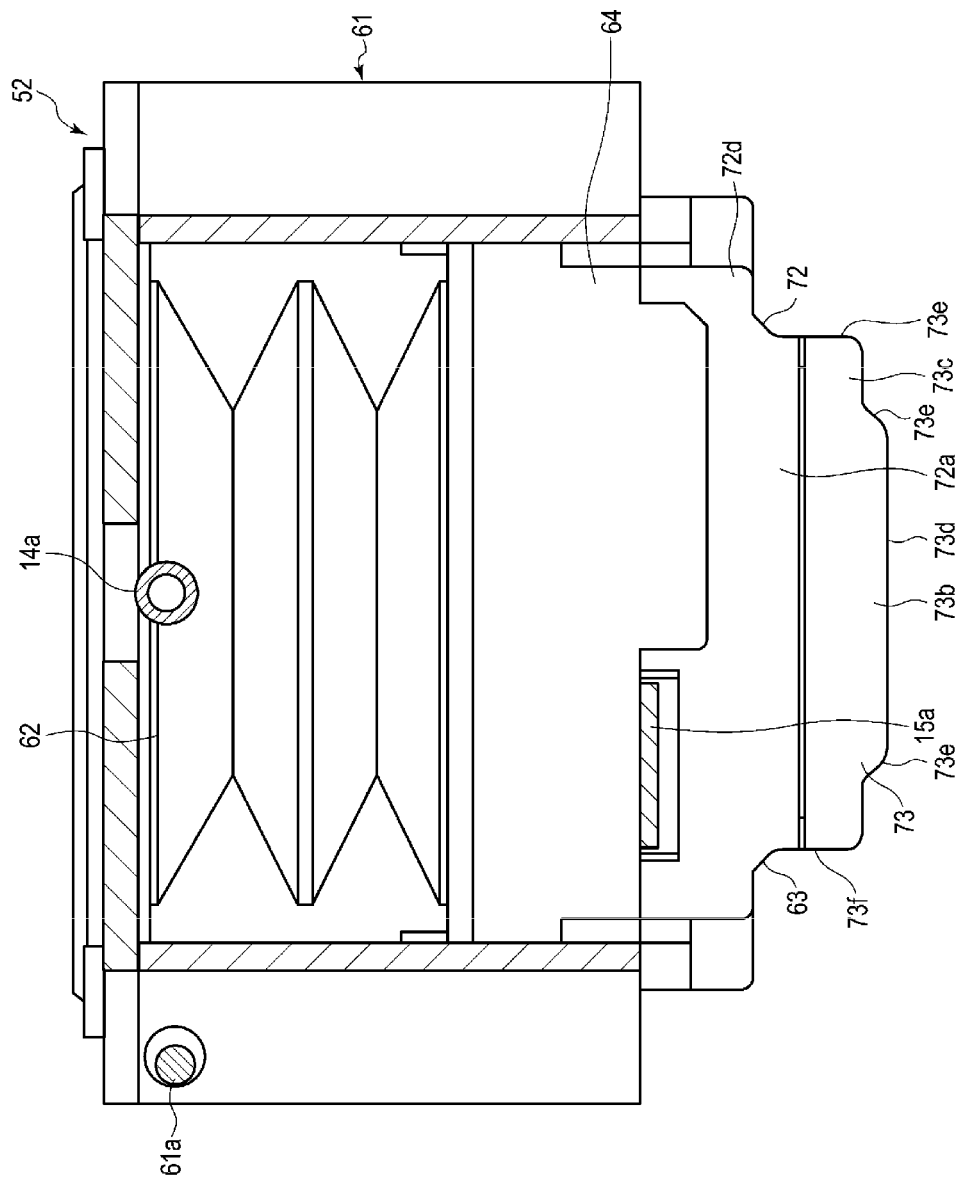

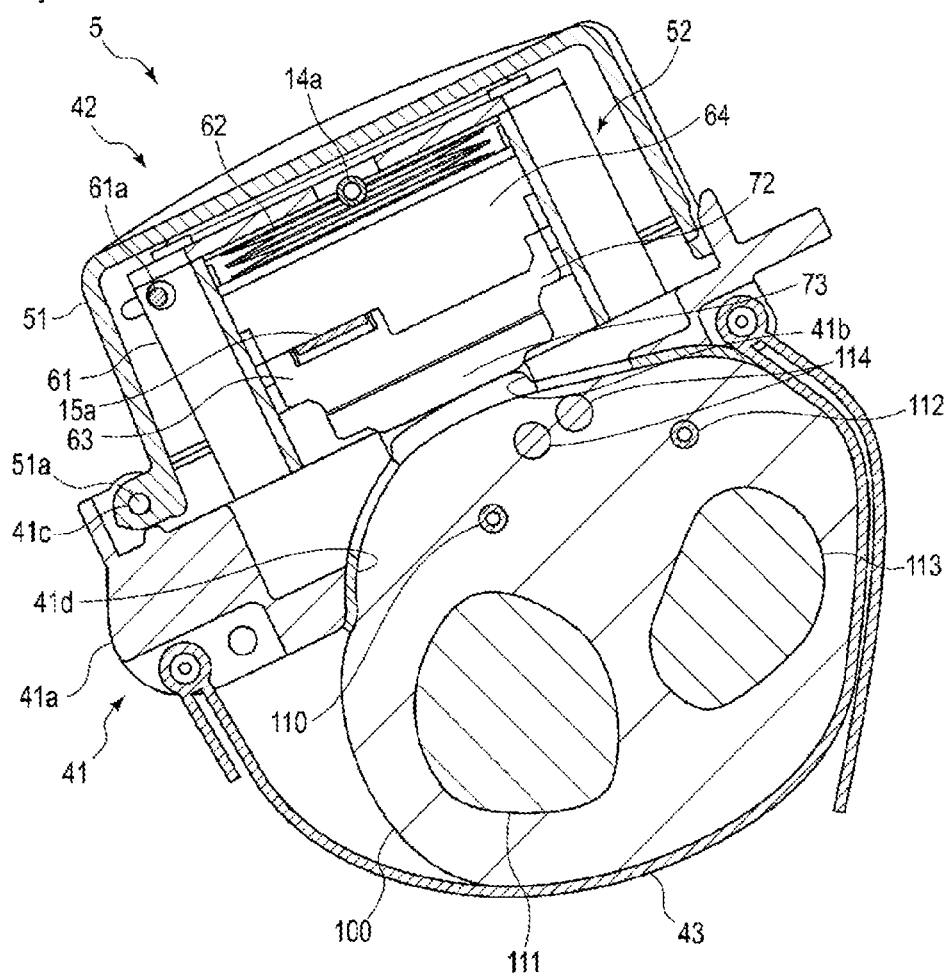
[FIG. 10]

[FIG. 11]
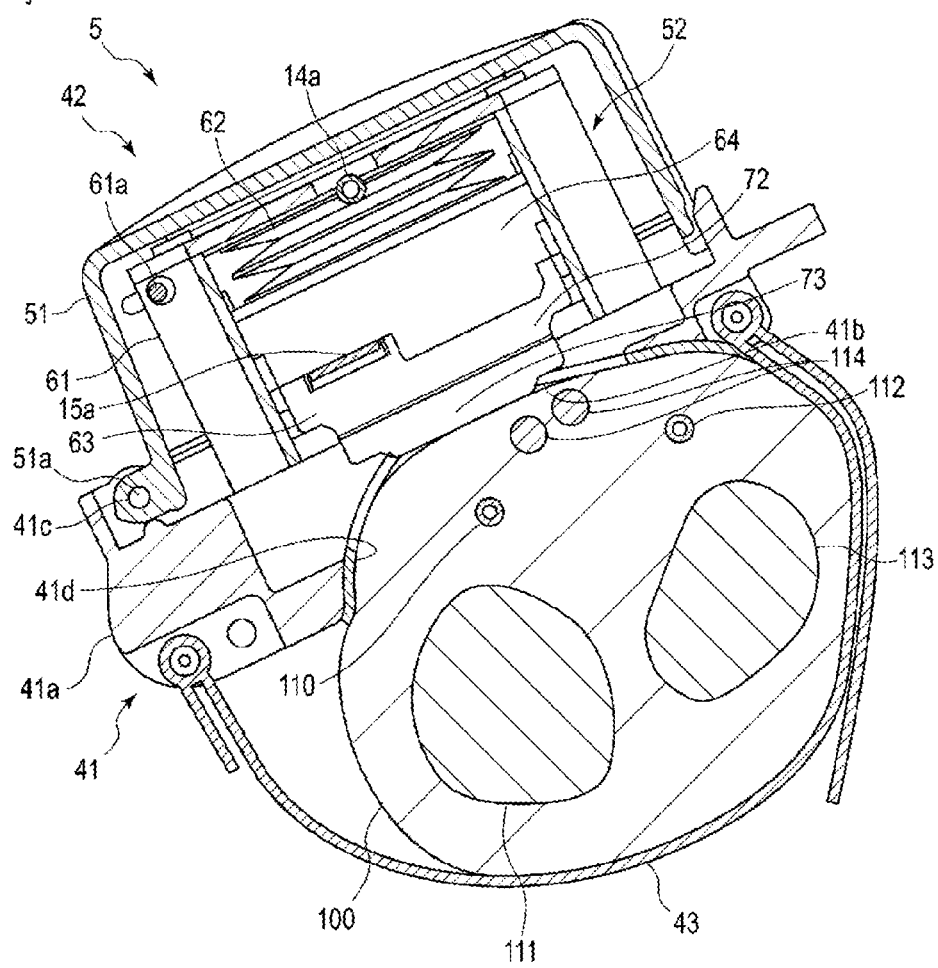

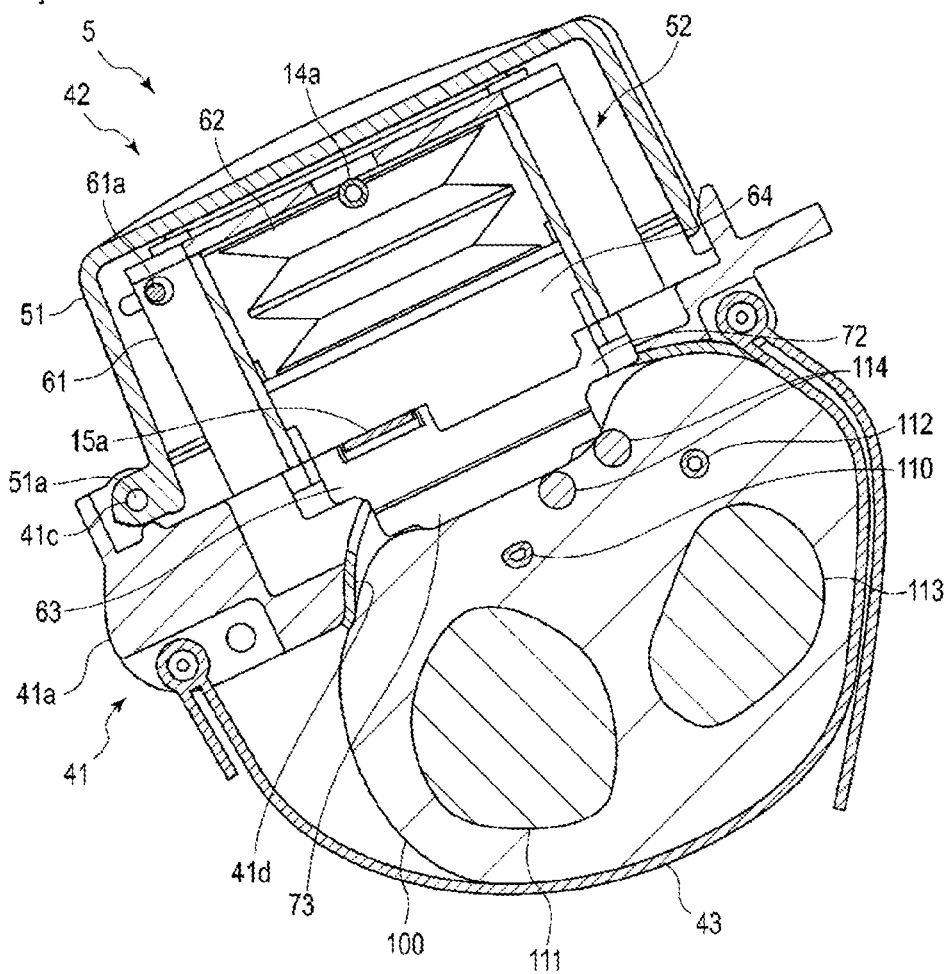
[FIG. 12]

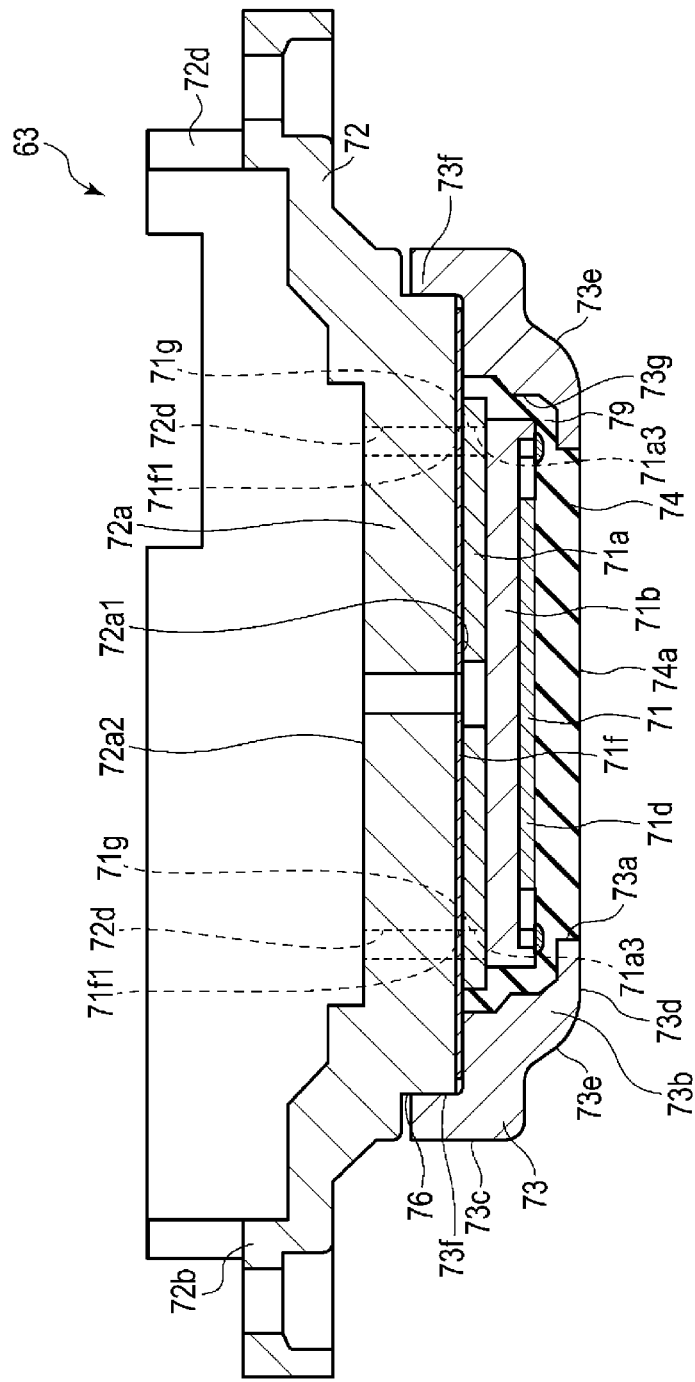
[FIG. 13]

[FIG. 14]
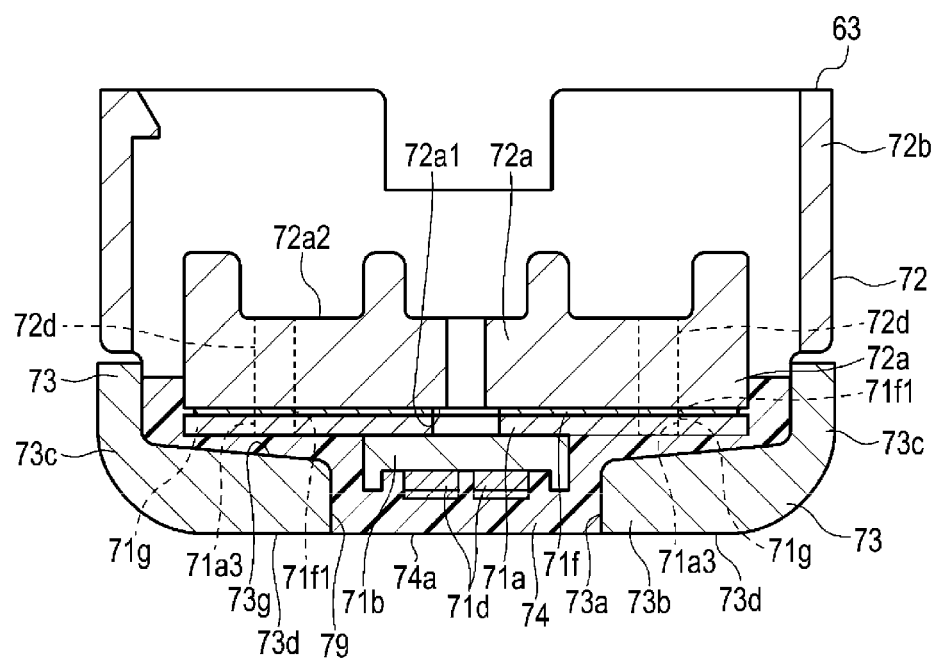

[FIG. 15]
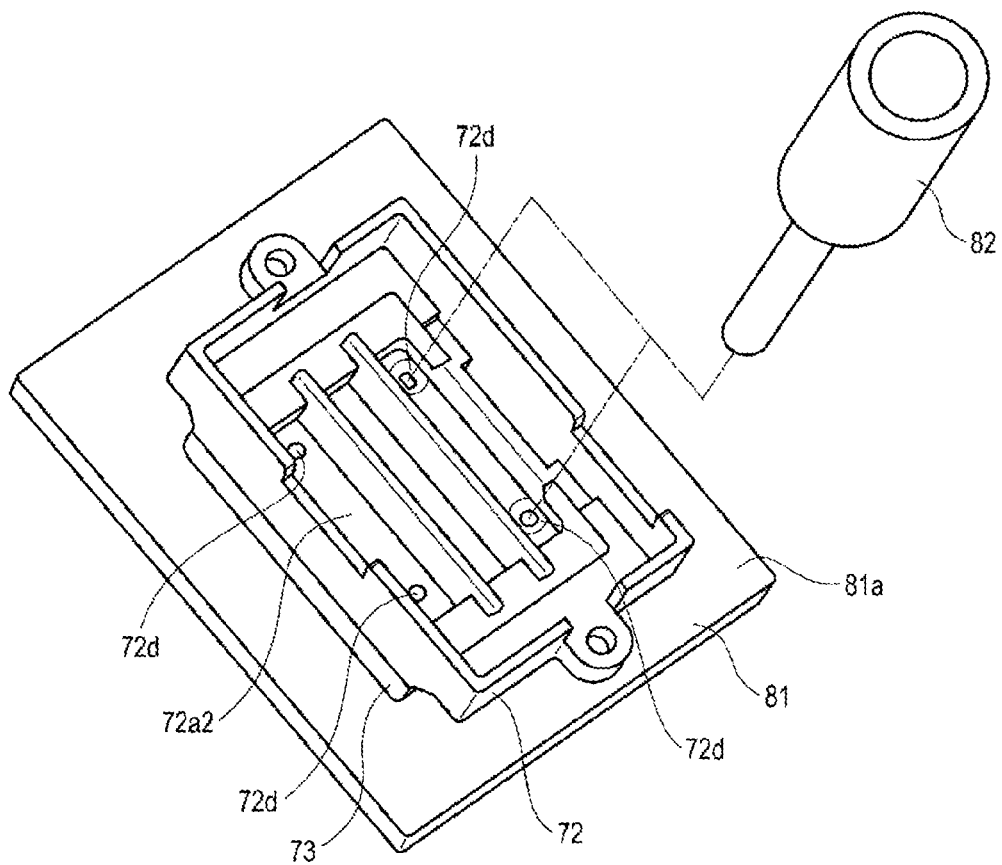

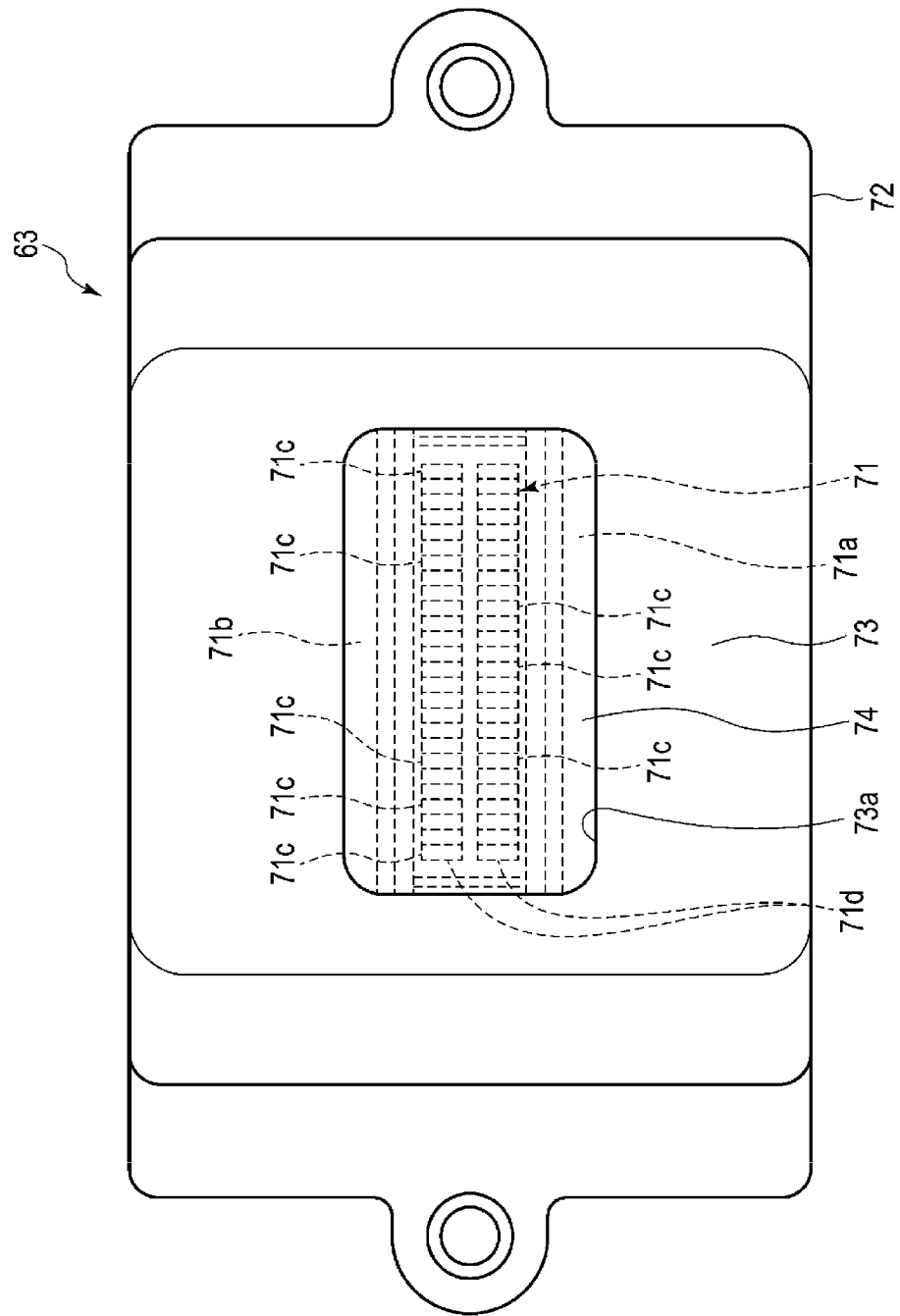
[FIG. 16]

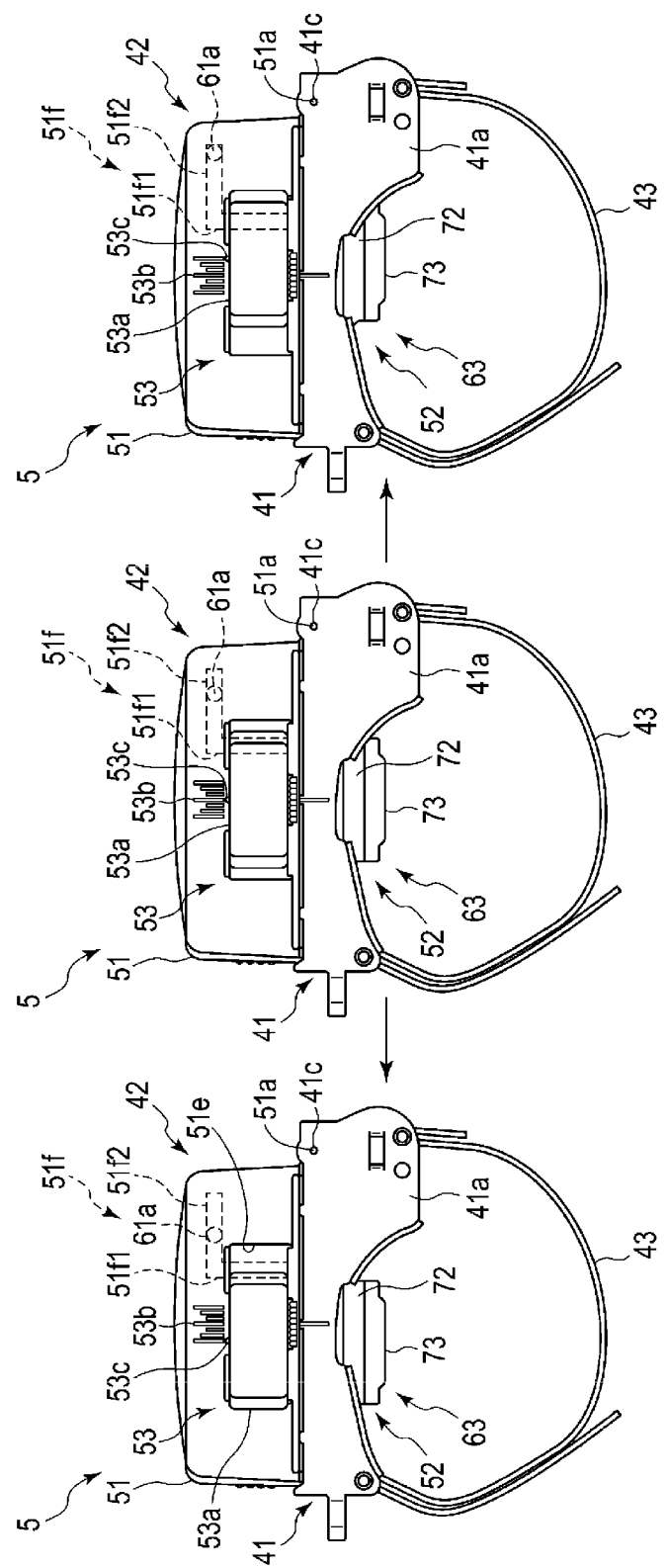
[FIG. 17]

[FIG. 18]
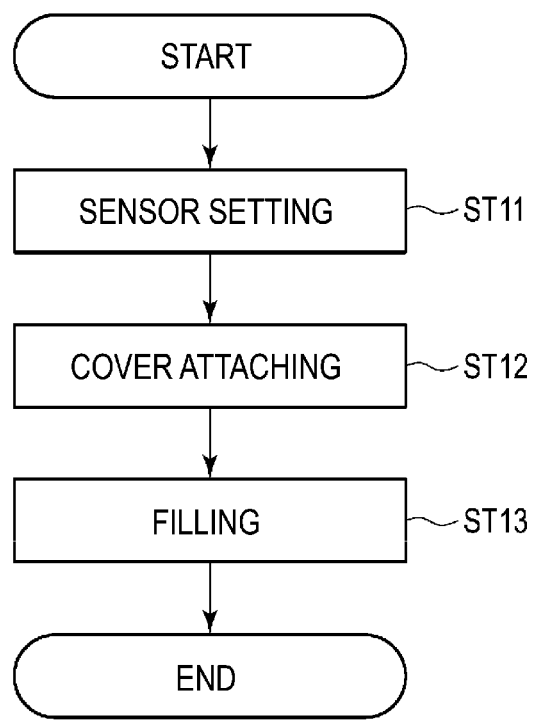

[FIG. 19]
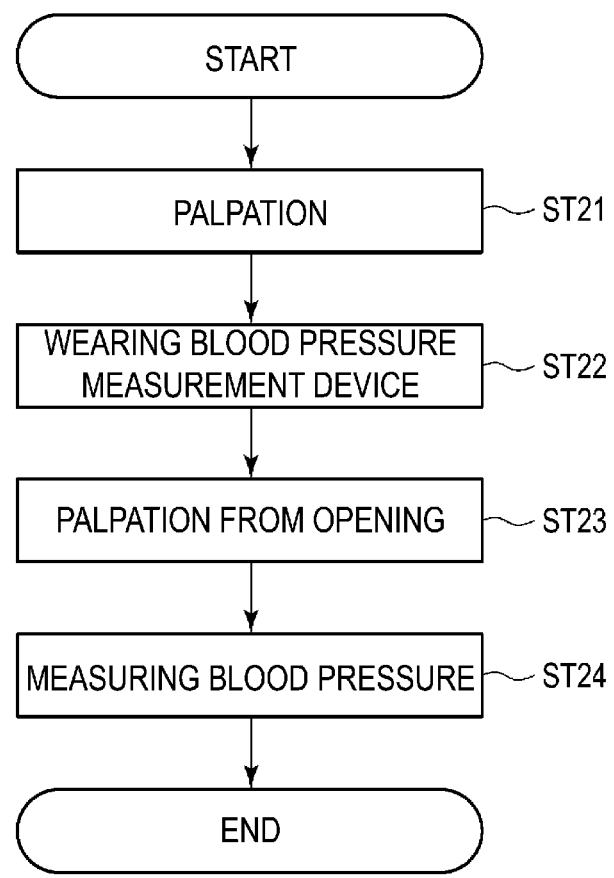

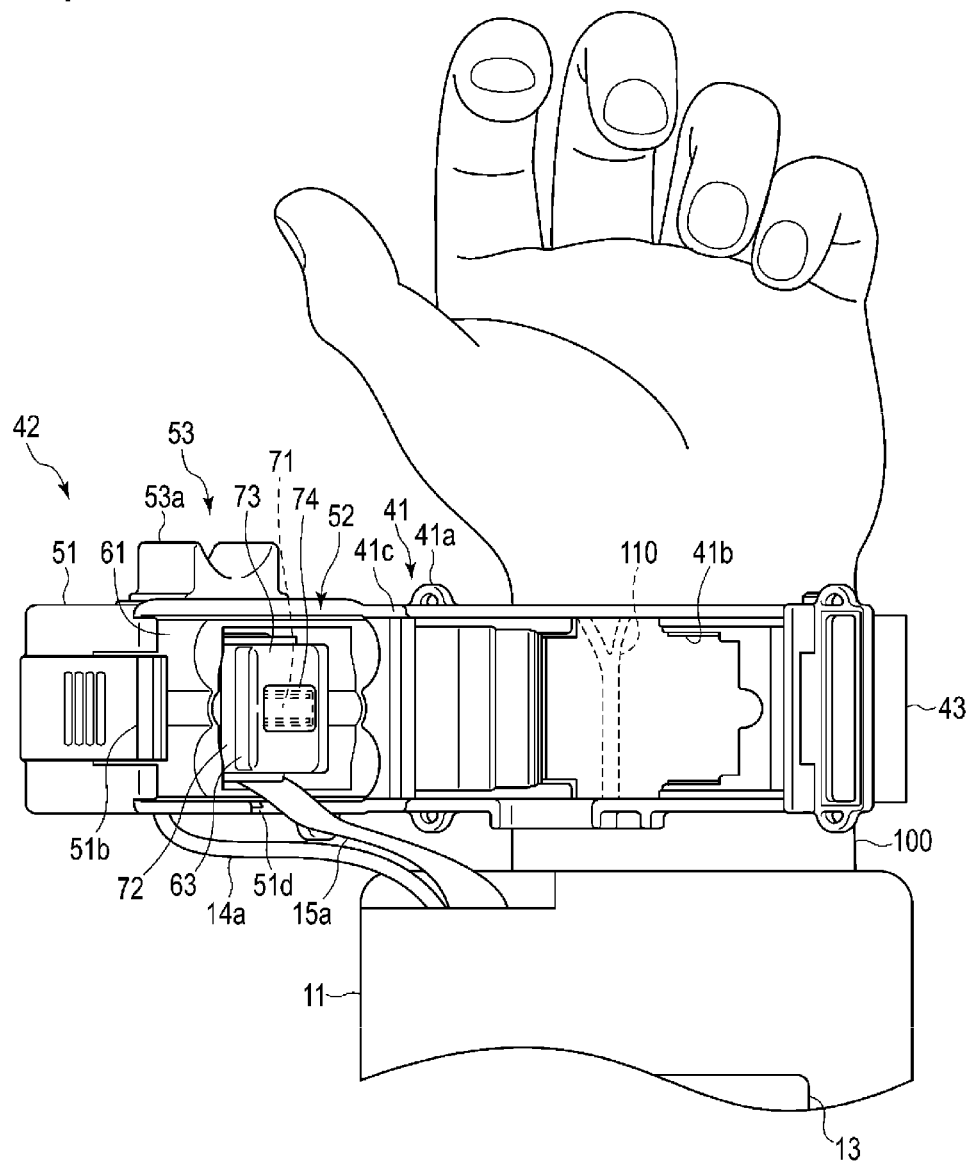
[FIG. 20]

[FIG. 21]
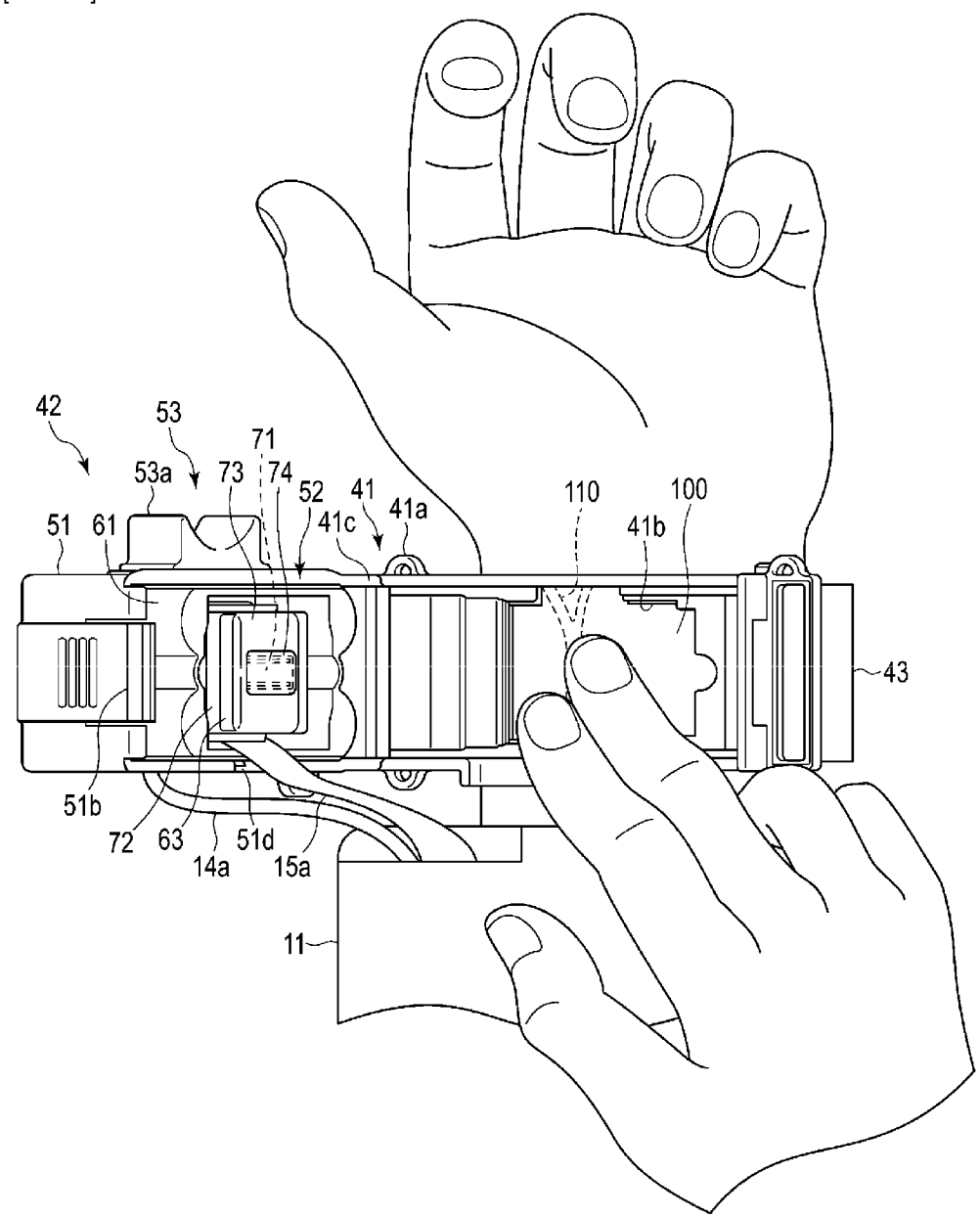

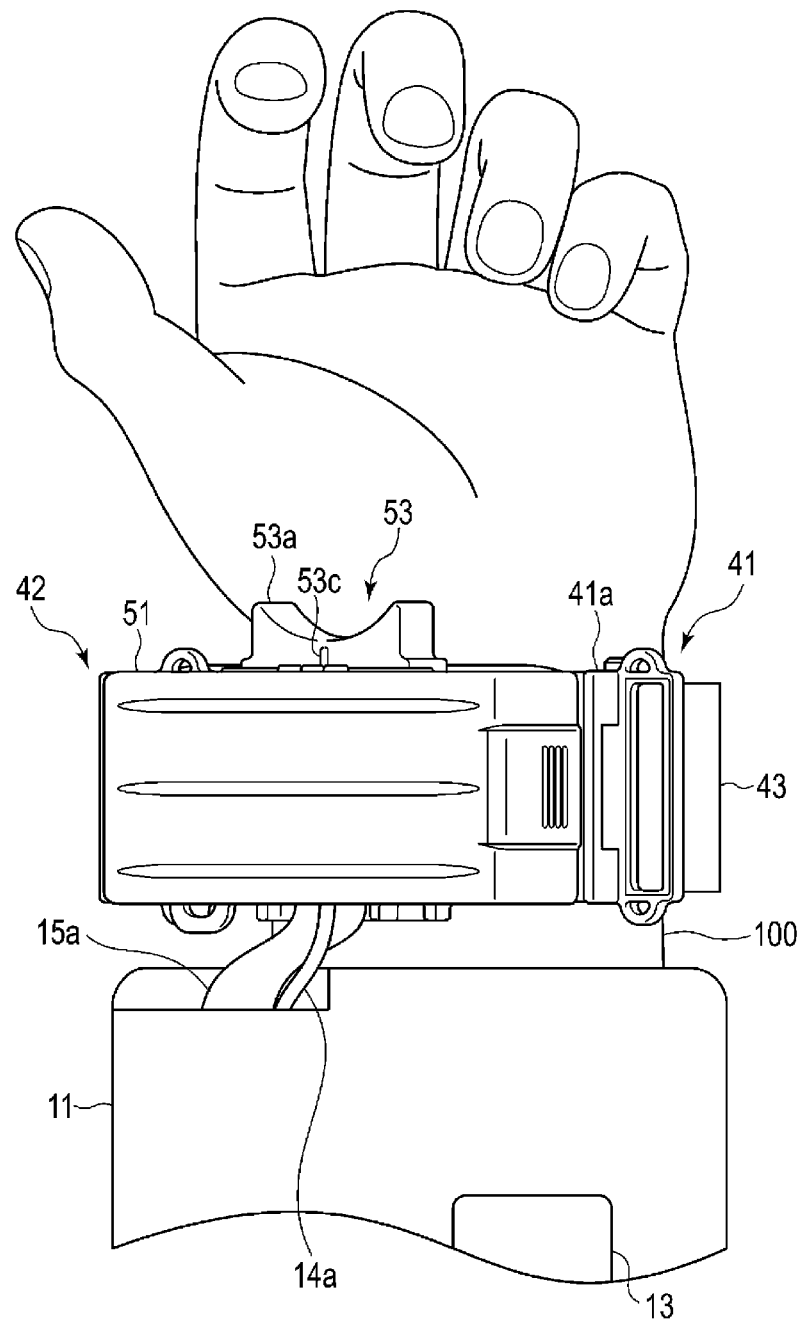
[FIG. 22]

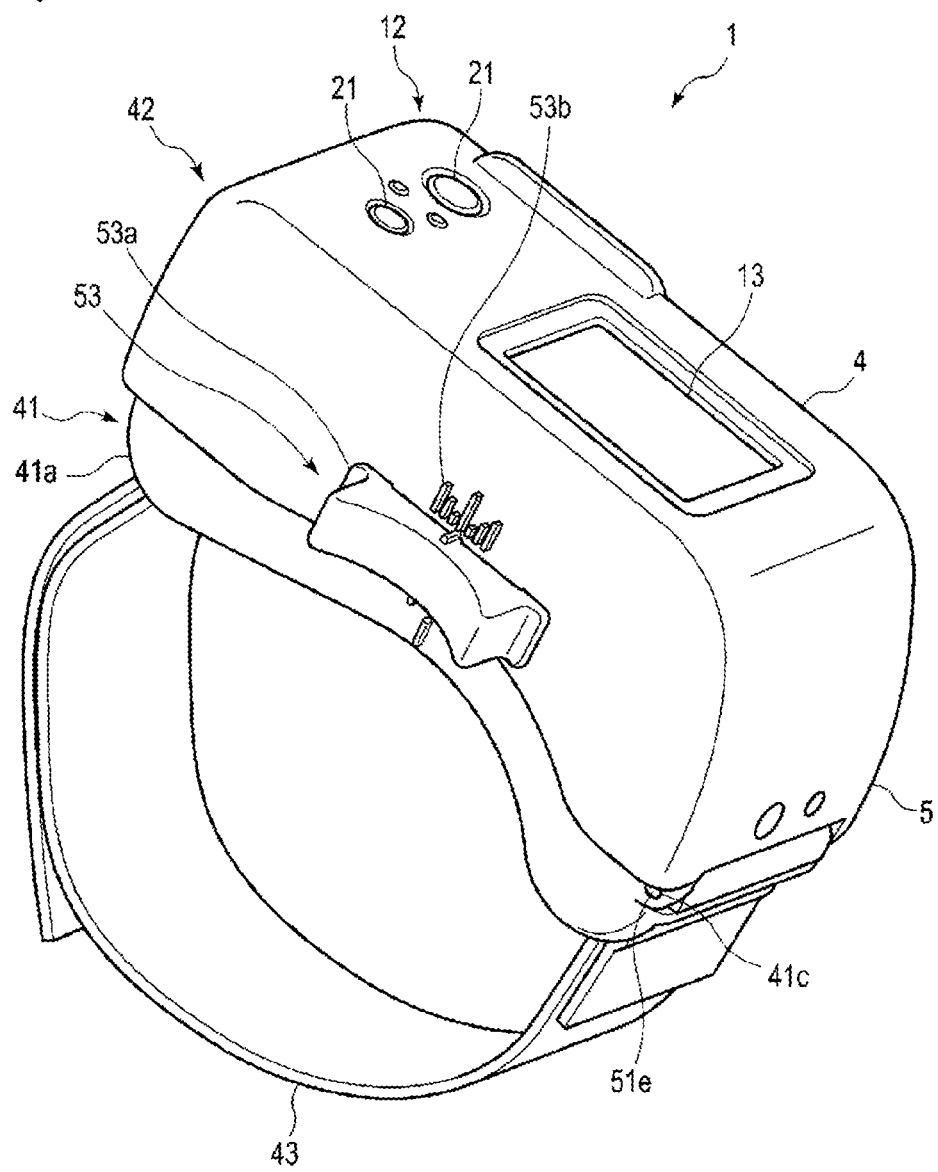
[FIG. 23]

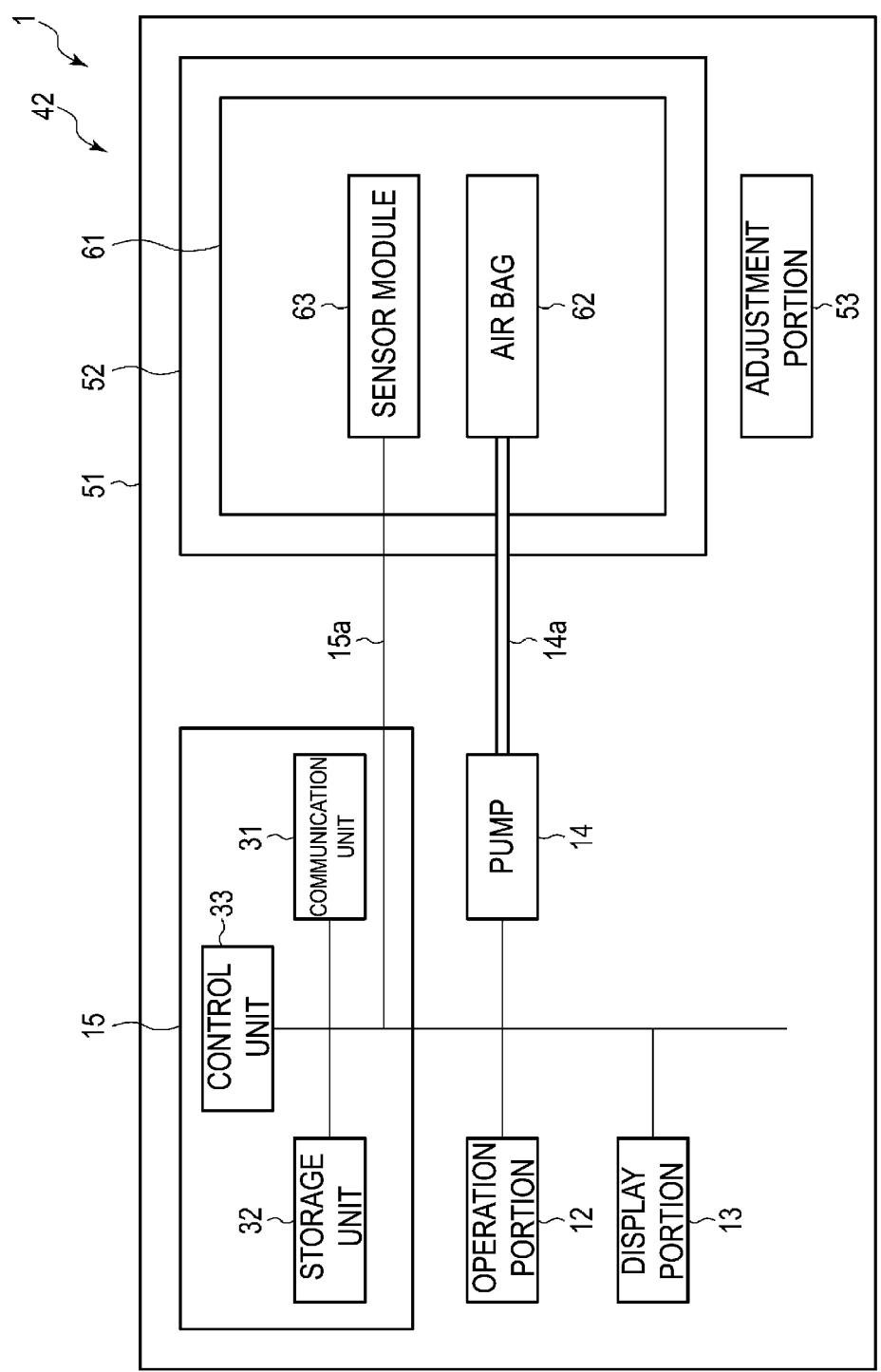

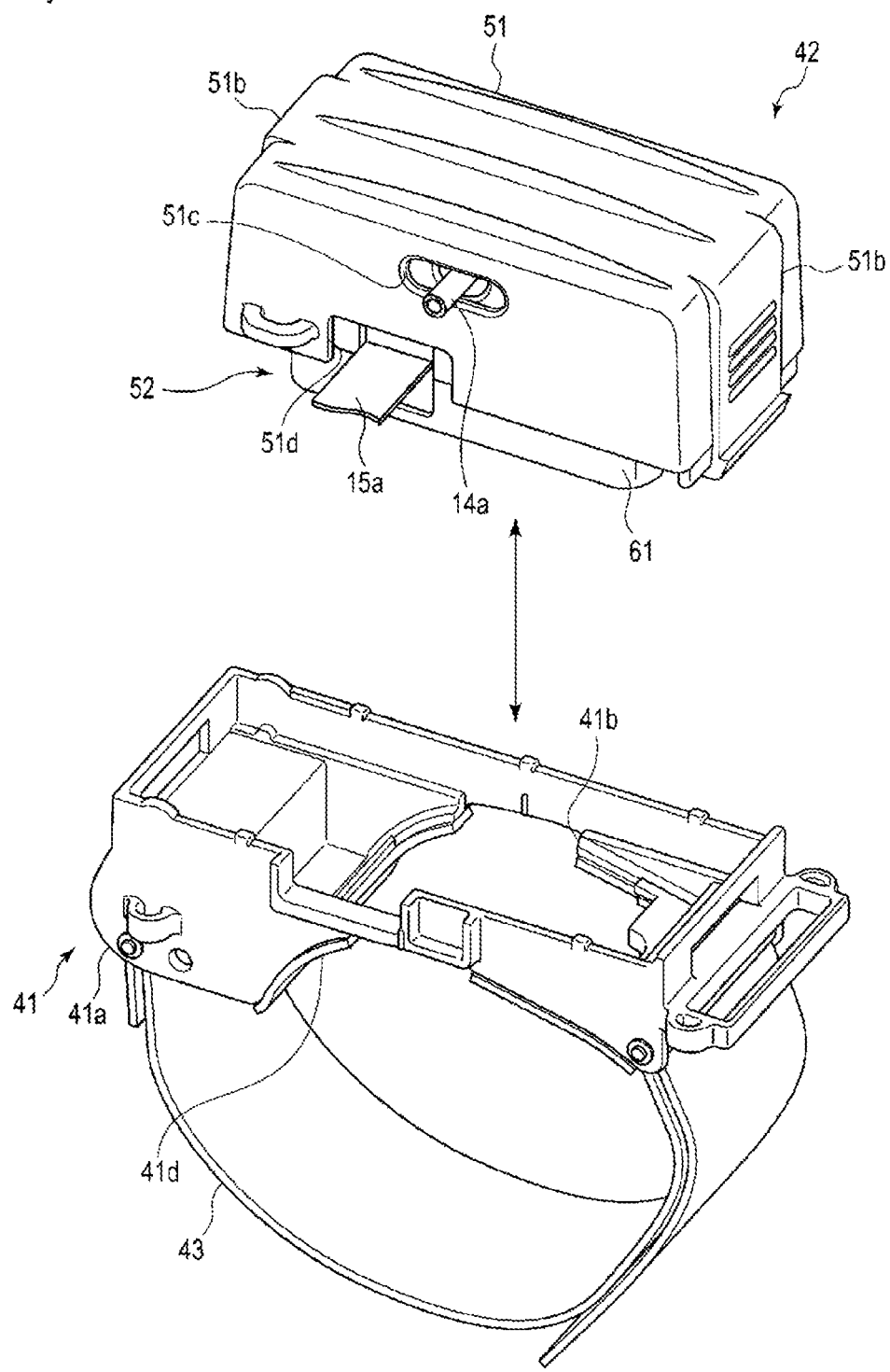
[FIG. 25]

SENSOR MODULE, METHOD FOR MANUFACTURING SENSOR MODULE, AND BLOOD PRESSURE MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2019/020044, filed May 21, 2019, which application claims priority from Japanese Patent Application No. 2018-099721, filed May 24, 2018, which applications are incorporated herein by reference in their entireties.

TECHNICAL FIELD

The present invention relates to a sensor module for measuring the pressure of a living body, a method for manufacturing a sensor module, and a blood pressure measurement device.

BACKGROUND ART

In recent years, blood pressure measurement devices for measuring blood pressure are being used to monitor health status at home, as well as in medical facilities. In such blood pressure measurement devices, for example, known technologies using the oscillometric method and the tonometry method are used. A blood pressure measurement device using the oscillometric method detects vibration of the artery wall and measures blood pressure by using pressure sensor to detect the pressure of a cuff wrapped around the upper arm or wrist of a living body. A blood pressure measurement device using the tonometry method measures blood pressure by bringing a sensor module including a plurality of pressure sensors into contact with the wrist in a region of the wrist where the artery is found.

CITATION LIST

Patent Literature

Patent Document 1: JP H1-288228 A

SUMMARY OF INVENTION

Technical Problem

Known technology relating to protecting a pressure sensor of a blood pressure measurement device using the tonometry method includes a technology in which an outer case body of a sensor module is composed of: a cover with an opening in a region opposite the pressure sensor; and a soft portion disposed in the opening of the cover.

This soft portion is formed on the pressure sensor by injecting a relatively soft resin material such as a silicone resin from the opening of the cover and is fixed on the inner surface of the cover including the inner surface of the opening. There is demand for a sensor module that comes into contact with a user when used, such as a sensor module used in a blood pressure measurement device that uses the tonometry method, to have a soft portion that is resistant to peeling off from an inner surface of a cover.

Thus, an object of the present invention is to provide a sensor module, a method for manufacturing a sensor module, and a blood pressure measurement device that can improve the holding force onto a soft portion.

Solution to Problem

An aspect provides a sensor module including:
a sensor base;
a pressure sensor portion fixed to the sensor base;
a sensor head cover including, on an outer surface, an opening in a region that comes into contact with a living body and an inner surface formed with unevenness, the sensor head cover being fixed to the sensor base and forming a gap portion that communicates with the opening between the inner surface, the sensor base, and the pressure sensor portion; and
a soft portion disposed in the gap portion and, at least, filling up the opening and covering the pressure sensor portion, the soft portion allowing pressure of the living body to transfer to the pressure sensor portion.

Here, the living body is a wrist, for example. According to this aspect, because the area of the inner surface of the housing portion is increased by the unevenness, the adhering surface between the inner surface of the housing portion and the soft portion can be increased. Thus, the adhesive strength between the inner surface and the soft portion is increased, and the holding force of the inner surface onto the soft portion is improved. This makes the soft portion resistant to peeling off from the inner surface.

A sensor module according to the sensor module of the aspect described above may be provided, wherein the unevenness of the inner surface is formed by roughening surface roughness.

According to this aspect, the holding force of the inner surface onto the soft portion can be improved.

A sensor module according to the sensor module of the aspect described above may be provided, wherein the inner surface is formed with leather-like grains.

According to this aspect, the holding force of the inner surface onto the soft portion can be improved.

A sensor module according to the sensor module of the aspect described above may be provided, wherein the region of the outer surface of the sensor head cover that comes into contact with the living body includes a flat surface portion formed as a flat surface with surface roughness less than the surface roughness of the inner surface; and the opening is formed in the flat surface portion.

According to this aspect, dirt and the like is less likely to adhere to the flat surface portion.

A sensor module according to the sensor module of the aspect described above may be provided, wherein the flat surface portion is provided with mirror surface processing.

According to this aspect, dirt and the like is even less likely to adhere to the flat surface portion. Furthermore, the feel felt by the user when the sensor module comes into contact with the living body can be even better.

A sensor module according to the sensor module of the aspect described above may be provided, wherein an entire region of the region of the outer surface of the sensor head cover that comes into contact with the living body has identical surface roughness.

According to this aspect, the feel felt by the user when the sensor module comes into contact with the living body can be even better.

A sensor module according to the sensor module of the aspect described above may be provided, wherein the sensor head cover is formed from ceramic.

According to this aspect, by forming the sensor head cover from a ceramic material, the surface roughness of the inner surface can be roughened by utilizing the surface roughness of the inner surface of the sensor head cover with no surface treatment having been provided. In other words, the inner surface of the sensor head cover that has not been provided with surface treatment includes the distinct unevenness of a ceramic material. This unevenness allows the surface roughness of the inner surface to be roughened.

Another aspect provides a method for manufacturing a sensor module including:
- fixing a pressure sensor portion to one main surface of a sensor base that includes a support wall portion in which a flow hole is formed extending through from the one main surface to another main surface;
- fixing a sensor head cover including: an opening in a flat surface portion of a region on an outer surface that comes into contact with a living body and an inner surface formed with unevenness to the sensor base and forming a gap portion that communicates with the flow hole between the inner surface, the sensor base, and the pressure sensor portion;
- closing off the opening with an opposing member by bringing the opposing member into contact with the flat surface portion;
- injecting a material for forming a soft portion into the flow hole from the other main surface; and
- separating the opposing member from the sensor head cover after the soft portion is formed from the material.

According to this aspect, the soft portion can be formed simply by injecting a predetermined amount of the material forming the soft portion into the flow hole to thus simply form the soft portion. Furthermore, the end surface of the soft portion can be formed flush with the flat surface portion of the sensor head cover.

Another aspect provides a blood pressure measurement device including:
- a sensor module including:
  - a sensor base;
  - a pressure sensor portion fixed to the sensor base;
  - a sensor head cover including, on an outer surface, an opening in a region that comes into contact with a living body and an inner surface formed with unevenness, the sensor head cover being fixed to the sensor base and forming a gap portion that communicates with the opening between the inner surface, the sensor base, and the pressure sensor portion; and
  - a soft portion disposed in the gap portion and, at least, filling up the opening and covering the pressure sensor portion, the soft portion allowing pressure of the living body to transfer to the pressure sensor portion;
- an attach portion including:
- an opening portion provided at a position opposite the living body, the sensor module being disposed in the opening portion, and
- an end surface that curves conforming to a shape in a circumferential direction of a portion of the living body;
- a fastener provided on the attach portion; and
- a case provided on the attach portion, the case housing the sensor module.

According to this aspect, in the sensor module, because the area of the inner surface of the housing portion is increased by the unevenness, the adhering surface between the inner surface of the housing portion and the soft portion can be increased. Thus, the adhesive strength between the inner surface and the soft portion is increased, and the holding force of the inner surface onto the soft portion is improved. This makes the soft portion resistant to peeling off from the inner surface.

Advantageous Effects of Invention

The present invention can provide a sensor module and a blood pressure measurement device in which the soft portion is resistant to peeling off.

BRIEF DESCRIPTION OF DRAWINGS

FIG. 1 is a perspective view illustrating the configuration of a blood pressure measurement device according to an embodiment of the present invention.

FIG. 2 is a block diagram illustrating the configuration of the blood pressure measurement device.

FIG. 3 is a perspective view illustrating the configuration of a sensor device of the blood pressure measurement device.

FIG. 4 is a perspective view illustrating the configuration of a portion of the sensor device of the blood pressure measurement device.

FIG. 5 is a perspective view illustrating the configuration of a sensor unit of the blood pressure measurement device.

FIG. 6 is a plan view illustrating the configuration of the sensor unit.

FIG. 7 is a cross-sectional view illustrating the configuration of a sensor module and an air bag of the sensor unit in a state of taken along a cross-section line VII-VII in FIG. 6.

FIG. 8 is a cross-sectional view illustrating the configuration of the sensor module and the air bag of the sensor unit in a state of taken along a cross-section line VIII-VIII in FIG. 6.

FIG. 9 is a cross-sectional view illustrating the configuration of the sensor module and the air bag of the sensor unit in a state of taken along a cross-section line IX-IX in FIG. 6.

FIG. 10 is a cross-sectional view illustrating the configuration of the blood pressure measurement device.

FIG. 11 is a cross-sectional view illustrating the configuration of the blood pressure measurement device.

FIG. 12 is a cross-sectional view illustrating the configuration of the blood pressure measurement device.

FIG. 13 is a cross-sectional view illustrating the configuration of the sensor module of the sensor unit.

FIG. 14 is a cross-sectional view illustrating the configuration of the sensor module.

FIG. 15 is a perspective view illustrating a sensor base of the sensor module.

FIG. 16 is a plan view illustrating the configuration of the sensor module of the sensor unit.

FIG. 17 is an explanatory diagram illustrating the position adjustment of the sensor unit of the blood pressure measurement device.

FIG. 18 is a flowchart illustrating an example of a method for manufacturing the sensor module.

FIG. 19 is a flowchart illustrating an example of blood pressure measurement using the blood pressure measurement device.

FIG. 20 is an explanatory diagram illustrating an example of blood pressure measurement using the blood pressure measurement device.

FIG. 21 is an explanatory diagram illustrating an example of blood pressure measurement using the blood pressure measurement device.

FIG. 22 is an explanatory diagram illustrating an example of blood pressure measurement using the blood pressure measurement device.

FIG. 23 is a perspective view illustrating the configuration of a blood pressure measurement device according to another embodiment of the present invention.

FIG. 24 is a block diagram illustrating the configuration of the blood pressure measurement device.

FIG. 25 is a perspective view illustrating the configuration of a blood pressure measurement device according to another embodiment of the present invention.

DESCRIPTION OF EMBODIMENTS

First Embodiment

An example of a blood pressure measurement device 1 according to the first embodiment of the present invention is described below using FIGS. 1 to 16.

FIG. 1 is a perspective view illustrating the configuration of the blood pressure measurement device 1 according to an embodiment of the present invention in a state in which a body fastener 16 is closed. FIG. 2 is a block diagram illustrating the configuration of the blood pressure measurement device 1. FIG. 3 is a perspective view illustrating the configuration of a sensor device 5 of the blood pressure measurement device 1 in a state in which a sensing body 42 is open. FIG. 4 is a perspective view illustrating the configuration of the blood pressure measurement device 1 with a sensor unit 52 removed from the sensor device 5. FIG. 5 is a perspective view illustrating the configuration of the sensor unit 52 of the blood pressure measurement device 1.

FIG. 6 is a plan view illustrating the configuration of the sensor unit 52. FIG. 7 is a cross-sectional view illustrating the configuration of a sensor module 63 and an air bag 62 of the sensor unit 52 in a state of taken along a cross-section line VII-VII in FIG. 6. FIG. 8 is a cross-sectional view illustrating the configuration of the sensor module 63 and the air bag 62 of the sensor unit 52 in a state of taken along a cross-section line VIII-VIII in FIG. 6. FIG. 9 is a cross-sectional view illustrating the configuration of the sensor module 63 and the air bag 62 of the sensor unit 52 in a state of taken along a cross-section line IX-IX in FIG. 6.

FIG. 10 is a cross-sectional view illustrating the configuration of the blood pressure measurement device 1. FIG. 11 is a cross-sectional view illustrating the configuration of the blood pressure measurement device 1. FIG. 12 is a cross-sectional view illustrating the configuration of the blood pressure measurement device 1. FIG. 13 is a cross-sectional view illustrating the configuration of the sensor module 63 of the sensor unit 52 in a state of taken along a cross-section aligned with the direction that pressure sensitive elements 71c of a pressure sensor portion 71 are arranged side by side. FIG. 14 is a cross-sectional view illustrating the configuration of the sensor module 63 in a state of taken along a cross-section orthogonal to the direction that pressure sensitive elements 71c are arranged side by side. FIG. 15 is a perspective view illustrating a sensor base 72 of the sensor module 63. FIG. 16 is a plan view illustrating the configuration of the sensor module 63 of the sensor unit 52.

Note that in the drawings, a radial artery of a wrist 100 is denoted as 110, a radius is denoted as 111, an ulnar artery is denoted as 112, an ulna is denoted as 113, and a tendon is denoted as 114.

The blood pressure measurement device 1 is an electronic blood pressure measurement device that is attached to the wrist 100 of a living body and calculates a blood pressure value from the pressure of the radial artery 110. As illustrated in FIGS. 1 to 16, the blood pressure measurement device 1 includes a device body 4 and the sensor device 5. For example, the blood pressure measurement device 1 has a configuration in which the sensor device 5 is attached to a region of the wrist 100 where the radial artery 110 is found and in which the device body 4 is attached to the wrist 100 adjacent to the sensor device 5 on the elbow side.

The blood pressure measurement device 1, by pressing the radial artery 110 with the sensor device 5, measures the pressure of the pressure pulse wave per heart beat that changes in conjunction with the heart rate of the radial artery 110, executes, via the device body 4, processing based on the tonometry method on the measured pressure, and obtains the blood pressure.

As illustrated in FIGS. 1 and 2, the device body 4 includes: a body case 11, an operation portion 12, a display portion 13, a pump 14, a control board 15, and the body fastener 16. Also, for example, the device body 4 may be provided with a cuff on the body fastener 16 that is configured to compress the wrist 100 during blood pressure measurement.

The body case 11 houses: a portion of the operation portion 12, a portion of the display portion 13, and the control board 15 and exposes: a portion of the operation portion 12 and a portion of the display portion 13 from the outer surface. In addition, the body fastener 16 is attached to the body case 11.

The operation portion 12 is configured to receive an instruction input from a user. For example, the operation portion 12 includes: a plurality of buttons 21 provided on the body case 11 and a sensor that detects operation of the buttons 21. Note that the operation portion 12 may be provided on the display portion 13 as a touch panel. When operated by the user, the operation portion 12 converts an instruction into an electrical signal. The sensor that detects operation of the buttons 21 is electrically connected to the control board 15 and outputs an electrical signal to the control board 15.

The display portion 13 is disposed in the body case 11 and is exposed from the outer surface of the body case 11. The display portion 13 is electrically connected to the control board 15. The display portion 13 is, for example, a liquid crystal display or an organic electroluminescent display. The display portion 13 displays various information including measurement results such as date and time; blood pressure values like maximum blood pressure and minimum blood pressure; heart rate; and the like.

The pump 14 is, for example, a piezoelectric pump. The pump 14 includes a tube 14a connected to the sensor device 5 for compressing air and supplying compressed air to the sensor device 5 via the tube 14a. The pump 14 is electrically connected to the control board 15.

As illustrated in FIG. 2, the control board 15 includes a communication unit 31, a storage unit 32, and a control unit 33, for example. The control board 15 is configured by the communication unit 31, the storage unit 32, and the control unit 33 being mounted on the board. Also, the control board 15 is connected to the sensor device 5 via a cable 15a. The cable 15a runs from inside the body case 11 to outside the body case 11 via a portion of the outer surface of the body case 11. For example, the cable 15a runs from inside the body case 11 to the sensor device 5 via an opening formed in a side surface of the body case 11.

The communication unit 31 is configured to transmit and receive information from an external device wirelessly or via a wire. The communication unit 31 transmits information, such as information controlled by the control unit 33, measured blood pressure values, pulse, and the like, to an external device via a network and receives a program for software update or the like from an external device via a network and sends this to the control unit.

In the present embodiment, the network is, for example, the Internet, but no such limitation is intended. The network may be a network such as a Local Area Network (LAN) provided in a hospital or may be a direct wired communication with an external device, using a cable or the like including terminals of a predetermined protocol such as USB. Thus, the communication unit 31 may include a plurality of wireless antennas, micro-USB connectors, or the like.

The storage unit 32 pre-stores: program data for controlling the entire blood pressure measurement device 1; settings data for configuring various functions of the blood pressure measurement device 1; calculation data for calculating blood pressure values and pulse from the pressure measured by the pressure sensitive elements 71*c*; and the like. Furthermore, the storage unit 32 stores information such as: the calculated blood pressure value; pulse; time series data in which this calculated data and time are associated; and the like.

The control unit 33 is composed of, for example, a single or a plurality of central processing units (CPU), controls the operation of the entire blood pressure measurement device 1, and executes each processing on the basis of the program data. The control unit 33 is electrically connected to the operation portion 12, the display portion 13, the pump 14, and the sensor device 5, controls the operation of each configuration, transmits and receive signals, and supplies power.

The body fastener 16 includes, for example, one or a plurality of band-like bands; and a fixing member such as a hook-and-loop fastener that secures the band wrapped around the wrist 100. The body fastener 16 fixes the body case 11 to the wrist 100.

With the device body 4 having such a configuration, by the control unit 33 executing processing using the program data stored in the storage unit 32, blood pressure data can be continuously formed from the pulse waves of the radial artery 110 detected by the sensor device 5. The blood pressure data includes data of blood pressure waveforms corresponding to the waveforms of measured pulse waves. The blood pressure data may further include time series data of a blood pressure feature value (blood pressure value). The blood pressure feature value includes, for example and without limitation, systolic blood pressure (SBP) and diastolic blood pressure (DBP). The maximum value in the pulse wave waveform per heart beat corresponds to systolic blood pressure, and the minimum value in the pulse wave waveform of per heart beat corresponds to diastolic blood pressure.

In this embodiment, the device body 4 measures the pressure pulse wave as a pulse wave by the tonometry method. Here, the tonometry method refers to a method for pressing the radial artery 110 from above the skin with appropriate pressure, forming a flat portion in the artery, and measuring the pressure pulse wave with the sensor device 5 in a balanced state between the interior and the exterior of the radial artery 110. According to the tonometry method, a blood pressure value per heart beat can be acquired.

As illustrated in FIGS. 1, 3, and 4, the sensor device 5 includes: an attach portion 41, the sensing body 42, and a fastener 43.

The attach portion 41 includes a main surface that has a shape that conforms to the circumferential direction of the wrist 100 in the region where the radial artery 110 of the left wrist 100 is found. As a specific example, the attach portion 41 includes: a base portion 41*a* that curves conforming to the shape in the circumferential direction of the wrist 100 in the region in contact with the wrist 100; an opening portion 41*b* formed in the base portion 41*a*, an attachment portion 41*c* provided on the base portion 41*a* for attaching the sensing body 42; and a cushion 41*d* provided on a main surface of the base portion 41*a* that comes into contact with the wrist 100.

The base portion 41*a* is configured to be elongated in one direction. The base portion 41*a* is disposed on a palm side of wrist 100 and on a side portion side on the radius 111 side of the wrist 100, and the main surface disposed on the wrist 100 side curves conforming to the shape in the circumferential direction of the palm side of the wrist 100 and the side portion side on the radius 111 side of the wrist 100. Furthermore, at least the outer circumferential edge side of the main surface of the base portion 41*a* comes into contact with the sensing body 42.

The opening portion 41*b* is provided in a central region of the base portion 41*a* and is formed with a size of one or a plurality of fingers. That is, the opening portion 41*b* is formed with a size that allows the region where the radial artery 110 of the wrist 100 is exposed from the opening portion 41*b* to be palpated by a finger, when the sensor device 5 is attached to the wrist 100, and that allows a portion of the sensing body 42 to come into contact with the wrist 100.

The attachment portion 41*c* is provided on a main surface of the base portion 41*a* opposite the surface facing the wrist 100 and provided on an end side of the base portion 41*a* in the longitudinal direction. The attachment portion 41*c* supports the sensing body 42 and is configured to move the sensing body 42 in a direction away from the base portion 41*a* and a direction toward the base portion 41*a*. As a specific example, the attachment portion 41*c* is a journal-like portion that rotatably journals the sensing body 42 about an axis. For example, the attachment portion 41*c* is integrally formed with the base portion 41*a*.

The cushion 41*d* is, for example, an elastic body configured in a sheet shape from a foaming resin material provided on a main surface of the base portion 41*a* that comes into contact with the wrist 100. The cushion 41*d* protects wrist 100 by elastically deforming, for example, when the blood pressure measurement device 1 is worn on the wrist 100.

As illustrated in FIGS. 2 to 12, the sensing body 42 includes: a case 51, the sensor unit 52, and an adjustment portion 53 for adjusting the position of the sensor unit 52.

The case 51 has a rectangular box shape with an open surface opposite the attach portion 41, for example. The case 51 supports the sensor unit 52 and the adjustment portion 53. Furthermore, the case 51 is attached to the attachment portion 41*c* in a manner to be movable back and forth in a direction away from the base portion 41*a*. As a specific example, the case 51 includes a rotation shaft 51*a* rotatably disposed in the attachment portion 41*c*. Also, the case 51 includes an engagement portion 51*b* that fixes the case 51 to the base portion 41*a* when it comes into contact with the base portion 41*a*. The engagement portion 51*b*, for example, is a projection that engages with an opening provided on the base portion 41*a* and, by being operated, is configured to release the engagement with the opening of the base portion 41*a*.

Furthermore, the case 51 includes: a first hole portion 51c where the tube 14a is disposed, a second hole portion 51d where the cable 15a is disposed, a third hole portion 51e that movably supports a portion of the adjustment portion 53, and a guide groove 51f that guides the movement of the sensor unit 52.

The first hole portion 51c and the second hole portion 51d are provided on the same side wall of the case 51 adjacent to the device body 4 when the device is worn on the wrist 100.

The third hole portion 51e is provided on a side wall opposite to the side wall of the case 51 where the first hole portion 51c and the second hole portion 51d are provided. The third hole portion 51e is a rectangular opening that linearly extends in the longitudinal direction of the case 51, or in other words, the circumferential direction of the wrist 100 when the sensor device 5 is attached to the wrist 100.

The guide groove 51f is provided on the inner surface side of the side wall of the case 51 provided with the third hole portion 51e. The guide groove 51f includes: a first groove 51f1 that extends from an opening end portion of the case 51 to partway toward the ceiling opposite the opening; and a second groove 51f2 that extends in a direction orthogonal to the first groove 51f1. The second groove 51f2 connects to the first groove 51f1 at one end and extends from this end to the other end toward one side in the longitudinal direction of the case 51.

The sensor unit 52 includes: a movable case 61, the air bag 62, the sensor module 63, and a movable base 64 that supports the sensor module 63 to be movable in one direction with respect to the movable case 61. The sensor unit 52 is supported by the case 51 in a manner to be movable in a predetermined range in the longitudinal direction of the case 51 via the adjustment portion 53.

The movable case 61 houses the sensor module 63 and the movable base 64 and supports the movable base 64 supporting the sensor module 63 in a manner allowing the movable base 64 to be movable toward the opening portion 41b of the attach portion 41. The movable case 61 is supported in a manner to be movable in the longitudinal direction of the case 51 inside the case 51.

As a specific example, the movable case 61 has a rectangular box shape with the surface opposite the attach portion 41 housing the air bag 62 and the sensor module 63 being open. The movable case 61 houses the air bag 62, the sensor module 63, and the movable base 64. In the movable case 61, the air bag 62 is disposed between the ceiling and the movable base 64. The movable case 61 supports the movable base 64 in a manner allowing the movable base 64 to be movable in one direction so that the sensor module 63 can protrude out from the opening of the movable case 61.

The movable case 61 includes: a guide projection 61a disposed on the outer surface of a side wall opposite the side wall on which the guide groove 51f of the case 51 is provided in a manner allowing the guide projection 61a to move in the guide groove 51f; and a fixing portion 61b in which a portion of the adjustment portion 53 is fixed. As the guide projection 61a moves in the second groove 51f2, the movable case 61 moves in the longitudinal direction of the case 51.

The air bag 62 has a bellows-like structure. The air bag 62 is fluidly connected to the pump 14 via the tube 14a. As illustrated in FIGS. 7 to 12, the air bag 62 expands in a direction from the ceiling of the movable case 61 toward the opening. When the air bag 62 expands, the sensor module 63 is moved from a position where the sensor module 63 is housed within the movable case 61 to a position where the sensor module 63 projects from the opening of the movable case 61 and comes into contact with the wrist 100 via the opening portion 41b of the attach portion 41. The air bag 62 is formed from polyurethane, for example.

As illustrated in FIGS. 13, 14, and 16, the sensor module 63 includes the pressure sensor portion 71, the sensor base 72 that supports the pressure sensor portion 71, a sensor head cover 73 that covers the sensor base 72 and including an opening 73a in a region opposite the pressure sensor portion 71, and a soft portion 74.

The sensor module 63 is disposed inside the movable case 61 and is supported by the movable case 61 in a manner allowing the sensor module 63 to move in a predetermined movement range in the direction of the ceiling and the opening of the movable case 61 opposing one another. In other words, the sensor module 63 is supported in a manner to be movable within the movable case 61, and the movement is restricted by a restriction portion such as a stopper or like when the sensor module 63 moves from the opening of the movable case 61 to the position where the sensor module 63 projects out a certain amount or more.

The pressure sensor portion 71 includes: a flexible substrate 71a, a substrate 71b mounted on the flexible substrate 71a, and the plurality of pressure sensitive elements 71c mounted on the substrate 71b. The pressure sensor portion 71 is fixed on one main surface of the sensor base 72.

The flexible substrate 71a is adhered and fixed on the sensor base 72 via an adhesive sheet 71f, for example. A predetermined circuit pattern is formed on one main surface of the flexible substrate 71a. The substrate 71b is mounted on the flexible substrate 71a. The cable 15a is connected to the circuit pattern of the flexible substrate 71a. The cable 15a is composed of a flexible substrate, for example. In other words, the flexible substrate 71a is electrically connected to the control board 15 via the cable 15a.

The substrate 71b is electrically connected to the flexible substrate 71a. The substrate 71b is electrically connected to the control board 15 via the flexible substrate 71a and the cable 15a. The substrate 71b has a rectangular plate-like shape.

The plurality of pressure sensitive elements 71c are mounted on the substrate 71b. The plurality of pressure sensitive elements 71c are electrically connected to the circuit pattern on the flexible substrate 71a. In other words, the plurality of pressure sensitive elements 71c are electrically connected to the control board 15 via the substrate 71b, the flexible substrate 71a, and the cable 15a.

The substrate 71b and the plurality of pressure sensitive elements 71c constitute a sensor chip. The plurality of pressure sensitive elements 71c are arranged in one direction, forming a pressure sensitive element array 71d. A single or a plurality of the pressure sensitive element arrays 71d are provided. In the case in which a plurality of the pressure sensitive element arrays 71d are provided, the plurality of pressure sensitive element arrays 71d are disposed at predetermined intervals in a direction orthogonal to the arrangement direction of the plurality of pressure sensitive elements 71c. In the present embodiment, two rows of the pressure sensitive element arrays 71d are formed.

Also, the pressure sensor portion 71 is disposed in the sensor base 72 such that the direction in which the plurality of pressure sensitive elements 71c are arranged is the width direction of the wrist 100. The pressure sensor portion 71 transmits a pressure value measured by the plurality of pressure sensitive elements 71c to the control board 15 via the cable 15a.

The sensor base 72 is made of a synthetic resin, for example. The sensor base 72 includes, integrally, a support wall portion 72a and a circumferential wall portion 72b vertically provided around the outer circumferential edge of the support wall portion 72a on the rear surface side on the opposite side to the living body. The sensor base 72 supports the pressure sensor portion 71 and the cable 15a connected to the pressure sensor portion 71.

The support wall portion 72a has a rectangular plate-like shape with a predetermined thickness. Here, the wrist 100 side of the support wall portion 72a is the front surface. The support wall portion 72a supports the pressure sensor portion 71 in a region, opposite the opening 73a of the sensor head cover 73, of a main surface 72a1 on the front surface side.

A groove portion 76 is formed at the outer edge portion of the main surface 72a1 on the wrist 100 side of the support wall portion 72a, with the support wall portion 72a projecting to the wrist 100 side. The groove portion 76 is formed in a manner allowing the sensor head cover 73 to be engaged with it. The pressure sensor portion 71 is fixed on the main surface 72a1 via the adhesive sheet 71f.

As illustrated in FIG. 15, a plurality of holes (flow holes) 72d are formed in the support wall portion 72a. The plurality of holes 72d extend through the support wall portion 72a in the thickness direction and open to the main surface 72a1 and another main surface 72a2.

The plurality of holes 72d are formed in a manner allowing the material of the soft portion 74 to flow through them. The number of holes 72d is four, for example. The holes 72d communicate with a gap portion 79 described below.

Note that in the present embodiment, the pressure sensor portion 71 is fixed to the main surface 72a1 of the support wall portion 72a, and a portion of the pressure sensor portion 71 is disposed opposite the holes 72d. Thus, in the present embodiment, a communication portion 71g that connects the holes 72d and the gap portion 79 is formed at a position where the holes 72d oppose the pressure sensor portion 71. The communication portion 71g is a hole, for example. In the present embodiment, the communication portion 71g includes: a hole 71f1 formed in the adhesive sheet 71f and a hole 71a3 formed in the flexible substrate 71a. Note that the communication portion 71g is not limited to being a hole. For example, it may be a cutout portion. Alternatively, the holes 72d may open to a position of the main surface 72a1 away from the pressure sensor portion 71. In this case, the communication portion 71g is not formed. As such, that the holes 72d communicate with the gap portion 79 includes the holes 72d communicating via the communication portion 71g and the holes 72d communicating directly.

The circumferential wall portion 72b is vertically provided around the outer circumference of the support wall portion 72a on the opposite side to the living body. The circumferential wall portion 72b is fixed to the movable base 64.

The sensor head cover 73 comes into contact with the wrist 100 at an end surface on the wrist 100 side. The opening 73a is formed in the end surface. The opening 73a is formed in a rectangular shape, for example. The sensor head cover 73 is formed from a synthetic resin material, for example.

The sensor head cover 73 includes, integrally, a protrusion portion 73b including the opening 73a; and a frame portion 73c vertically provided around the circumferential edge of the protrusion portion 73b on the sensor base 72 side. At least a portion of the opposing surfaces of the sensor head cover 73 and the sensor base 72 are separated from one another, and the gap portion 79 is formed between an inner surface 73g of the sensor head cover 73 and the sensor base 72 and the pressure sensor portion 71.

In the present embodiment, as illustrated in FIGS. 13 and 14, the gap portion 79 is formed between the main surface 72a1 of the support wall portion 72a on which the pressure sensor portion 71 is mounted and the inner surface of the protrusion portion 73b on the pressure sensor portion 71 side, and the gap portion 79 is formed between the outer circumferential surface of the support wall portion 72a and the inner circumferential surface of the frame portion. The gap portion 79 communicates with the plurality of holes 72d.

The protrusion portion 73b has a rectangular plate-like shape, for example. An end surface (flat surface portion) 73d, which is the main surface of the protrusion portion 73b on the living body side, is formed with a flat surface. The end surface 73d corresponds to a portion of the region of the outer surface of the sensor module 63 that comes into contact with the wrist 100 when the blood pressure measurement device 1 is in use.

Also, the protrusion portion 73b includes the end surface 73d and a circumferential surface 73e formed continuously with the end surface 73d. The circumferential surface 73e is a surface that follows the thickness direction of the protrusion portion 73b. An edge portion between the circumferential surface 73e and the end surface 73d is formed with a curved surface. A corner portion of the circumferential surface 73e is formed with a curved surface. The edge portion between the circumferential surface 73e and the end surface 73d; and a portion of the circumferential surface 73e correspond to portions of the region of the outer surface of the sensor module 63 that comes into contact with the wrist 100 when the blood pressure measurement device 1 is in use. When the end surface 73d of the sensor head cover 73 is pressed against the wrist 100, a portion of the protrusion portion 73b digs into the wrist 100, putting the end surface 73d, the edge portion of the end surface 73d and the circumferential surface 73e, and a portion of the circumferential surface 73e into contact with the wrist 100.

Note that the region of the outer surface of the sensor head cover 73 that comes into contact with the wrist 100 changes depending on the shape of the sensor head cover 73 and the pressing force from the sensor head cover 73 against the wrist 100. In the present embodiment, because the sensor head cover 73 has a configuration including the protrusion portion 73b, for example, the end surface 73d, the edge portion between the end surface 73d and the circumferential surface 73e, and a portion of the circumferential surface 73e are regions of the outer surface of the sensor head cover 73 that come into contact with wrist 100.

The outer surface roughness of the outer surface of the sensor head cover 73 that constitutes the region that comes into contact with the wrist 100 is less than the surface roughness of the inner surface 73g of the sensor head cover 73 that constitutes the gap portion 79. In other words, the surface roughness of the inner surface 73g is greater than the outer surface roughness of the outer surface of the sensor head cover 73 that constitutes the region that comes into contact with the wrist 100.

Specifically, in the present embodiment, the surface roughness of the end surface 73d and the surface roughness of the edge portion between the end surface 73d and the circumferential surface 73e, and the surface roughness of the portion of the circumferential surface 73e are less than the surface roughness of the inner surface 73g. In the present embodiment, the surface roughness of the regions of the outer surfaces of the sensor head cover 73 that comes into contact with the wrist 100 are identical. For example, the surface roughness of the entire outer surface of the sensor head cover 73 may be less than the surface roughness of the inner surface 73g of the sensor head cover 73.

The end surface 73d, the edge portion of the end surface 73d and the circumferential surface 73e, and the portion of the circumferential surface 73e corresponding to the region of the outer surface of the sensor head cover 73 that comes into contact with the wrist 100 are provided with mirror surface processing. For example, in another example, the entire outer surface of the sensor head cover 73 is provided with mirror surface processing.

Also, an engagement portion 73f that engages with the groove portion 76 of the sensor base 72 is provided at one end of the frame portion 73c on the sensor base 72 side.

The inner surface 73g is composed of: the inner surface of the opening 73a, the surface of the protrusion portion 73b on the pressure sensor portion 71 side, and the inner surface of the frame portion 73c.

The inner surface 73g has unevenness. As an example, the inner surface 73g is given unevenness by making the surface roughness rough. The surface roughness of the inner surface 73g is surface roughness that causes the area of the inner surface 73g to be an area that can improve the holding force holding the soft portion 74.

The surface roughness of the inner surface 73g can be roughened by using a mold with rough surface roughness to form the sensor head cover 73, for example. Alternatively, the surface roughness of the inner surface 73g can be roughened by providing a predetermined surface processing on the inner surface 73g. As a predetermined processing, for example, the surface roughness of the inner surface 73g may be roughened by a chemical, by applying the chemical to the inner surface 73g.

Alternatively, the sensor head cover 73 may be formed from ceramic. By forming the sensor head cover 73 from ceramic, the surface roughness of the inner surface 73g can be roughened by utilizing the surface roughness of the inner surface 73g with no surface treatment having been provided.

In addition, in the present embodiment, the surface roughness of the inner surface 73g is rougher than the surface roughness of the end surface 73d where the opening 73a of the sensor head cover 73 is formed.

The soft portion 74 is provided in the gap portion 79. The soft portion 74 at least is disposed inside the opening 73a and covers the pressure sensor portion 71 and is configured to allow the pressure of the radial artery 110 to transfer to the pressure sensor portion 71.

In the present embodiment, as illustrated in FIG. 13, the soft portion 74 is disposed in a range of the gap portion 79 from the opening 73a to the adhesive sheet 71f, for example. Note that, as illustrated in FIG. 13, a portion of the sensor head cover 73 is in contact with the adhesive sheet 71f and that, as illustrated in FIG. 14, another portion thereof is not in contact with the adhesive sheet 71f. Therefore, as illustrated in FIG. 14, a portion of the soft portion 74 is located at a position over the adhesive sheet 71f.

Because the soft portion 74 is disposed in a range of the gap portion 79 from the opening 73a to the adhesive sheet 71f, the soft portion 74 fills the opening 73a; the flexible substrate 71a, the substrate 71b, and all of the pressure sensitive elements 71c of the pressure sensor portion 71 are covered by the soft portion 74; and the soft portion 74 is adhered in the range of the inner surface 73g opposing the pressure sensor portion 71.

As illustrated in FIG. 15, for example, the soft portion 74 is formed by injecting a relatively soft resin material such as a silicone resin into the gap portion 79 via the holes 72d from the main surface 72a2 side. When the resin material is injected, a smooth surface 81a of an opposing plate 81 is brought into contact with the end surface 73d, and the opening 73a is closed off. An end surface 74a that comes into contact with the wrist 100 of the soft portion 74 is formed conforming to the smooth surface 81a of the opposing plate 81. In other words, the surface roughness of the end surface 74a is managed by the smooth surface 81a. Thus, the surface roughness of the smooth surface 81a is set on the basis of the surface roughness required for the end surface 74a.

The end surface 74a of the soft portion 74 is formed flush with the end surface 73d of the sensor head cover 73. Note that it is sufficient that the soft portion 74 comes into contact with the wrist 100 and is formed from a material that allows the pressure of the radial artery 110 to be detected by the pressure sensitive elements 71c, and the thickness, shape that comes into contact with the wrist 100, and material of the soft portion 74 can be selected as appropriate.

As illustrated in FIG. 17, the adjustment portion 53 is configured to adjust the position of the sensor unit 52, with respect to the case 51, in the circumferential direction of the wrist 100. The adjustment portion 53 is located on the outer surface of the case 51 and includes an adjustment catch 53a, the portion of which is fixed to the fixing portion 61b of the movable case 61 via the third hole portion 51e. Also, the adjustment portion 53 includes: graduations 53b provided adjacent to the third hole portion 51e of the case 51 and an instruction portion 53c provided on the adjustment catch 53a that indicates the graduations 53b.

The adjustment catch 53a is connected to the sensor unit 52 by being fixed to the movable case 61. The adjustment catch 53a is configured to move the sensor unit 52. In other words, the adjustment portion 53 is an adjustment mechanism that, by the adjustment catch 53a being moved in the longitudinal direction of the third hole portion 51e, moves the sensor unit 52 along the second groove 51f2 and adjusts the position of the sensor unit 52 with respect to the case 51.

The graduations 53b and the instruction portion 53c are display portions that display the position of the adjustment catch 53a, i.e., the position of the sensor unit 52 connected to the adjustment catch 53a, in a visually recognizable manner.

The fastener 43 includes, for example, one or a plurality of band-like bands and a fixing member such as a hook-and-loop fastener that secures the band wrapped around the wrist 100. The fastener 43 fixes the attach portion 41 and the sensing body 42 to the wrist 100. Note that the fastener 43 may be composed of: a first belt referred to as a parent that includes a buckle; and a second belt referred to as a pointed end that is fixed to the buckle. Also, the fastener 43 may further have a configuration in which the case 51 is fixed to the attach portion 41 by the fastener 43 being wrapped around the case 51.

In other words, the fastener 43 is configured to prevent the case 51 from moving in a direction away from the attach portion 41 when the reaction force, when the sensor module 63 presses against the wrist 100 due to the expansion of the air bag 62, acts on the movable case 61 and when the case 51 is directly pressed by the movable case 61 or indirectly pressed via the adjustment catch 53a from the movable case 61.

Next, an example of a method for manufacturing the sensor module 63 will be described using FIG. 18. FIG. 18 is a flowchart illustrating an example of a method for manufacturing the sensor module 63. The method for manufacturing the sensor module 63 includes: a sensor setting step of setting the pressure sensor portion 71 on the sensor base 72 (step ST11), a cover attaching step of attaching the sensor head cover 73 to the sensor base 72 (step ST12), and a filling step of supplying the material that forms the soft portion 74 with the opening 73*a* closed off by the opposing plate 81 and filling the material to a position where the pressure sensor portion 71 in the gap portion 79 is covered (step ST13).

First, in the sensor setting step (step ST11), the plurality of pressure sensitive elements 71*c* are mounted on the substrate 71*b*. Next, the substrate 71*b* on which the plurality of pressure sensitive elements 71*c* are mounted is mounted on the flexible substrate 71*a*. In this way, the pressure sensor portion 71 is completed. Next, the pressure sensor portion 71 is fixed on the sensor base 72 via the adhesive sheet 71*f*.

Then, in the cover attaching step (step ST12), the sensor head cover 73 is put on the sensor base 72. At this time, the pressure sensor portion 71 is disposed in an area corresponding to the opening 73*a* of the sensor head cover 73. Also, the gap portion 79 is formed between the sensor base 72 and the sensor head cover 73.

Next, the filling step (step ST13) is performed. In the filling step, the integral body of the sensor base 72 and the sensor head cover 73 in an assembled state is orientated so that the opening 73*a* faces down in the direction of gravity, and the opening 73*a* is closed off by the smooth surface 81*a* of the opposing plate 81. The smooth surface 81*a* of the opposing plate 81 is formed with surface roughness set on the basis of the surface roughness required for the end surface 74*a* of the soft portion 74.

In this state, a nozzle 82 through which a soft resin material, i.e., the material of the soft portion 74, flows is inserted into the holes 72*d* from the main surface 72*a*2 side and a predetermined amount of the material of the soft portion 74 is supplied via the holes 72*d*. The material flows into the gap portion 79 from the holes 72*d* due to gravity and reaches the opening 73*a*.

The material of the soft portion 74 supplied into the gap portion 79, including the opening 73*a*, forms the soft portion 74. After the soft portion 74 is formed, the opposing plate 81 is removed at a predetermined timing. Note that, depending on the type of material of the soft portion 74, the soft portion 74 may be formed by cooling or heating. Furthermore, after removing the opposing plate 81, the end surface 74*a* of the soft portion 74 may be subjected to surface treatment.

In this manner, the sensor module 63 is completed.

Next, an example of measurement of a blood pressure value using the blood pressure measurement device 1 will be described using FIGS. 19 to 22. FIG. 19 is a flowchart illustrating an example of blood pressure measurement using the blood pressure measurement device 1, illustrating both the operation of the user and the operation of the control unit 33. FIGS. 20 to 22 are explanatory diagrams illustrating an example of blood pressure measurement using the blood pressure measurement device 1.

First, the user searches by palpating the wrist 100 for the position of the radial artery 110 (step ST21). For example, at this time, a visible line may be drawn on the skin above the radial artery 110 with a pen.

The user then separates the sensing body 42 of the sensor device 5 from the attach portion 41. In the present embodiment, the user operates the engagement portion 51*b* to release the engagement of the case 51 with the base portion 41*a* and rotates the sensing body 42 about the rotation shaft 51*a* in a direction away from the attach portion 41.

The user then attaches the device body 4 and the sensor device 5 as illustrated in FIG. 20 (step ST22). As a specific example, the user first passes the wrist 100 through the body fastener 16 of the device body 4 and the fastener 43 of the sensor device 5 and places the device body 4 and the sensor device 5 at a predetermined position on the wrist 100. Next, the body fastener 16 of the device body 4 is tightened, and the device body 4 is fixed to the wrist 100. Here, in a case of configuration in which a cuff is provided on the body fastener 16 of the device body 4, a check is performed to see whether the skin of the wrist 100 is caught in the body fastener 16 (cuff) and whether the body fastener 16 (cuff) is too loose is performed. Next, the position of the sensor device 5 is adjusted so that the opening portion 41*b* of the attach portion 41 of the sensor device 5 is located at the radial artery 110 of the wrist 100. In addition, the user tightens the fastener 43 of the sensor device 5, and the sensor device 5 is fixed to the wrist 100, with the radial artery 110 held at the position of the opening portion 41*b*.

Next, as illustrated in FIG. 21, the user palpates the wrist 100 from the opening portion 41*b* of the attach portion 41 (step ST23) and checks again that the radial artery 110 is located at the opening portion 41*b*. Then, as illustrated in FIG. 22, the user rotates the sensing body 42 in a direction toward the attach portion 41 and fixes the sensing body 42 to the attach portion 41 via the engagement portion 51*b*. Note that when the position of the sensing body 42 is misaligned with the radial artery 110, the adjustment catch 53*a* is operated to adjust the position of the sensing body 42.

Next, the user operates the operation portion 12 to send an instruction to measure the blood pressure. The control unit 33 measures the blood pressure on the basis of the blood pressure measurement instruction (step ST24). At this time, the control unit 33 drives and controls the pump 14, and as illustrated in FIGS. 7 to 12, the air bag 62 is expanded, moving the sensor module 63 progressively toward the wrist 100 from a state of being housed inside the movable case 61, and the sensor head cover 73 and the soft portion 74 of the sensor module 63 are pressed against the region where the radial artery 110 of the wrist 100 is found. By pressing the sensor head cover 73 and the soft portion 74 against this region of the wrist 100, the radial artery 110 is pressed with an appropriate amount of pressure so that a portion of the radial artery 110 is flattened. In this state, the pressure sensitive elements 71*c* of the pressure sensor portion 71 measure the pressure pulse waves.

Note that the control unit 33 obtains the blood pressure via the tonometry method from the pressure pulse waves of the radial artery 110 detected by the pressure sensor portion 71. Note that prior to blood pressure measurement, the control unit 33 may perform a blood pressure measurement for calibration on the basis of program data stored in the storage unit 32 or may perform a check to determine whether or not the worn state of the device body 4 and/or the sensor device 5 and the position of the pressure sensor portion 71 are correct.

According to the blood pressure measurement device 1 configured in this way, the inner surface 73*g* of the sensor head cover 73 can be given unevenness to increase the area. As a result, the adhesion area between the inner surface 73*g* and the soft portion 74 can be increased, which improves the holding force of the inner surface 73*g* onto the soft portion 74. Thus, with the blood pressure measurement device 1, the soft portion 74 can be made resistant to peeling off from the inner surface 73*g*.

Furthermore, by roughening the surface roughness of the inner surface 73g and giving the inner surface 73g unevenness, the surface area of the inner surface 73g can be increased and the holding force onto the soft portion 74 can be improved.

Furthermore, by making the surface roughness of the end surface 73d of the sensor head cover 73 less than the surface roughness of the inner surface 73g, dirt and the like is less likely to adhere to the end surface 73d. Furthermore, when manufacturing the soft portion 74, in the case in which a small amount of material that forms the soft portion 74 leaks from between the opening 73a and the opposing plate 81, for example, the material that forms the soft portion 74 adhered to the end surface 73d can be easily peeled off.

Furthermore, because the surface roughness of the end surface 73d is less than the surface roughness of the end surface 73g, the feel felt by the user when the sensor module 63 is pressed against the wrist 100 when the blood pressure measurement device 1 is in use can be good.

Furthermore, because the end surface 73d is a surface that has been provided with mirror surface processing, dirt and like is even less likely to adhere to the end surface 73d. Furthermore, when manufacturing the soft portion 74, in the case in which a small amount of material that forms the soft portion 74 leaks from between the opening 73a and the opposing plate 81, for example, the material of the soft portion 74 adhered to the end surface 73d can be more easily removed. Furthermore, the feel felt by the user when the sensor module 63 is pressed against the wrist 100 can be better.

Furthermore, because the surface roughness of the entire region of the outer surface of the sensor head cover 73 that comes into contact with the wrist 100 has identical surface roughness, i.e., the identical surface roughness to the end surface 73d, the feel felt by the user when the sensor module 63 is pressed against the wrist can be better.

Also, by forming the sensor head cover 73 from a ceramic material, the surface roughness of the inner surface 73g can be roughened by utilizing the surface roughness of the inner surface 73g of the sensor head cover 73 with no surface treatment having been provided.

Furthermore, because the soft portion 74 is manufactured by injecting material from the hole 72d using the opposing plate 81, the soft portion 74 can be manufactured via a simple process. Furthermore, by simply injecting the material, the end surface 74a of the soft portion 74 can be formed flush with the end surface 73d of the sensor head cover 73.

Additionally, the attach portion 41 is provided with the large opening portion 41b through which palpation is possible, and, because the wrist 100 can be palpated with the sensor device 5 worn in this state, whether or not the sensor device 5 is worn at the predetermined position can be easily determined. In other words, the wrist 100 can be palpated from the opening portion 41b, and, when the sensor device 5 of the blood pressure measurement device 1 is worn on the wrist 100, the sensor device 5 is worn in an ad-lib state on the wrist 100 and the radial artery 110 is found by palpation; thereafter, the sensor device 5 is adjusted in position and worn properly. As a result, the blood pressure measurement device 1 can be easily worn at the appropriate position. In addition, because the sensor device 5 has a configuration that includes the adjustment portion 53, the adjustment catch 53a can be operated even after the sensor device 5 is worn properly on the wrist 100. This allows the position of the sensor unit 52 with respect to the radial artery 110 to be adjusted, which further allows the pressure of the radial artery 110 to be measured at a suitable position.

Furthermore, the sensor device 5 has a configuration in which the sensing body 42 is configured to be moved in a direction away from the attach portion 41 and in which the sensing body 42 rotates away from the attach portion 41 about an axis. Thus, when the sensing body 42 is moved, the sensor module 63 provided on the sensing body 42 moves in a direction away from the opening portion 41b of the attach portion 41.

This can prevent the sensor module 63 from moving while in contact with the wrist 100 and the attach portion 41 when the sensing body 42 is moved with respect to the attach portion 41. Specifically, the sensor unit 52 measures the blood pressure, with the sensor head cover 73 and the soft portion 74 of the sensor module 63 projecting from the opening of the movable case 61, at a position where the wrist 100 can be appropriately pressed via the air bag 62.

Even when the sensing body 42 is moved with respect to the attach portion 41 in this state, in the sensing body 42, the sensor module 63 moves in a direction away from the wrist 100. Thus, the sensing body 42 cannot move in a state of the end surface of the sensor head cover 73 and the soft portion 74 being in contact with the wrist 100 or the attach portion 41. As a result, when the sensing body 42 is moved, damage caused by the sensor module 63 interfering other configurations or the wrist 100 and a load on the wrist 100 can be prevented.

In this way, because the sensor device 5 is provided with the opening portion 41b with a shape that allows palpation through the attach portion 41 and the sensing body 42 is configured to move in a direction away from the attach portion 41 and the wrist 100, damage to the sensor module 63 can be prevented and safety can be improved.

Furthermore, the sensor device 5 has a configuration in which the sensing body 42 is rotated about an axis with respect to the attach portion 41. Thus, a simple configuration can be achieved, with the attachment portion 41c provided on the attach portion 41 and with the rotation shaft 51a journaled in the attachment portion 41c provided on the sensing body 42. Thus, compared to a configuration in which the sensor device 5 is slid in a direction with respect to the attach portion 41, a simpler configuration which is cheaper to manufacture can be achieved.

Also, the sensor device 5 has a configuration in which the sensing body 42 rotates with respect to the attach portion 41 at one end side in the longitudinal direction of the attach portion 41. Thus, substantially the entire region of the upper surface of the attach portion 41 can be exposed to the outside. As a result, the opening portion 41b of the attach portion 41 is completely exposed, allowing the size of the shape of the opening portion 41b required for palpation to be kept as small as possible. Furthermore, because a rail configuration for sliding the sensing body 42 with respect to the attach portion 41 or a configuration for supporting the sensing body 42 on the attach portion 41 after sliding are not necessary, the shape in the width direction of the wrist 100 of the sensor device 5 can be kept as small as possible. This allows the sensor device 5 to be made compact.

As described above, according to the blood pressure measurement device 1 according to the embodiment of the present invention, because the inner surface 73g of the sensor head cover 73 is configured to have unevenness, the area of the inner surface 73g is increased and the contact area between the inner surface 73g and the soft portion 74 is increased. Thus, the holding force of the inner surface 73g onto the soft portion 74 can be improved. Thus, with the blood pressure measurement device 1, the soft portion 74 can be made resistant to peeling off from the inner surface 73g.

Note that the present invention is not limited to the embodiment described above. In the example described above, the blood pressure measurement device 1 has a configuration in which the surface roughness of the inner surface 73g is roughened to give the inner surface 73g unevenness. However, no such limitation is intended. In other examples, the inner surface 73g may have leather-like grains.

A method of giving the inner surface 73g leather-like grains includes using a mold provided with graining processing to form leather-like grains on the sensor head cover 73. Alternatively, the inner surface 73g may be provided with graining processing to have leather-like grains. Alternatively, as described above, the inner surface 73g may have leather-like grains and the surface roughness of the inner surface 73g may be roughened.

Alternatively, the inner surface 73g may have unevenness other than leather-like grains. As an example, protrusion portions such as ribs and bosses may be formed on the inner surface 73g. By forming protrusion portions in this manner, the area of the inner surface 73g is increased.

Note that the present invention is not limited to the embodiment described above. In the example described above, the blood pressure measurement device 1 has a configuration in which the device body 4 and the sensor device 5 are different bodies. However, no such limitation is intended. For example, as illustrated in FIGS. 23 and 24, the blood pressure measurement device 1 may have a configuration in which the device body 4 and the sensor device 5 are integrally formed. The blood pressure measurement device 1 with such a configuration, for example, may have configuration in which the operation portion 12, the display portion 13, the pump 14, and the control board 15 used in the device body 4 are provided in the case 51 of the sensing body 42.

Also, in the example described above, the blood pressure measurement device 1 has a configuration in which the sensing body 42 moves in a direction away and a direction toward the attach portion 41 by the sensing body 42 rotating with respect to the attach portion 41 about an axis. However, no such limitation is intended. For example, as illustrated in FIG. 25, the blood pressure measurement device 1 may have a configuration in which the sensing body 42 moves in a direction away and a direction toward the attach portion 41 by the attach portion 41 and the sensing body 42 being separated. In the case in which the blood pressure measurement device 1 has this configuration, the engagement portions 51b are provided at a plurality of positions on the case 51 of the sensing body 42, and the sensing body 42 engages with the attach portion 41 at these positions.

Also, in the examples described above, the blood pressure measurement device 1 has a configuration that measures the pressure of the radial artery 110 and that obtains the blood pressure by the tonometry method. However, no such limitation is intended. In another example, the pressure of the ulnar artery 112 is measured. The blood pressure measurement device 1 may also have a configuration in which the blood pressure is obtains via a method other than the tonometry method. In other words, as long as the blood pressure measurement device 1 has a configuration in which the sensor module 63 that comes into contact with the wrist 100 is configured to move with respect to the opening portion 41b of the attach portion 41 and the wrist 100 and in which the sensing body 42 moves while in contact with and the wrist 100 or in other configurations, another blood pressure measurement method may be used.

In the examples described above, the opening portion 41b of the attach portion 41 allows for palpation. However, no such limitation is intended. The opening portion 41b may be an opening that does not allow palpation.

In other words, the embodiments described above are merely examples of the present invention in all respects. Of course, various modifications and variations can be made without departing from the scope of the present invention. Thus, specific configurations in accordance with an embodiment may be adopted as appropriate at the time of carrying out the present invention.

REFERENCE SIGNS LIST

1 Blood pressure measurement device
4 . . . Device body
5 . . . Sensor device
11 . . . Body case
12 . . . Operation portion
13 . . . Display portion
14 . . . Pump
14a . . . Tube
15 . . . Control board
15a . . . Cable
16 . . . Body fastener
21 . . . Button
31 . . . Communication unit
32 . . . Storage unit
33 . . . Control unit
41 . . . Attach portion
41a . . . Base portion
41b . . . Opening portion
41c . . . Attachment portion
42 . . . Sensing body
43 . . . Fastener
51 . . . Case
51a . . . Rotation shaft
51b . . . Engagement portion
51c . . . First hole portion
51d . . . Second hole portion
51e . . . Third hole portion
51f . . . Guide groove
51f1 . . . First groove
51f2 . . . Second groove
52 . . . Sensor unit
53 . . . Adjustment portion
53b . . . Graduations
53c . . . Instruction portion
61 . . . Movable case
61a . . . Guide projection
61b . . . Fixing portion
62 . . . Air bag
63 . . . Sensor module
71 . . . Pressure sensor portion
71a . . . Flexible substrate
71b . . . Substrate
71c . . . Pressure sensitive element
72 . . . Sensor base
72a . . . Support wall portion
72b . . . Circumferential wall portion
72d . . . Hole
73 . . . Sensor head cover
73a . . . Opening
73b . . . Protrusion portion
73c . . . Frame portion 73d . . . End surface
73e . . . Circumferential surface
73g . . . Inner surface
74 . . . Soft portion
74a . . . End surface
79 . . . Gap portion
81 . . . Opposing plate (opposing member)
81a . . . Smooth surface
82 . . . Nozzle
100 . . . Wrist
110 . . . Radial artery
111 . . . Radius
112 . . . Ulnar artery
113 . . . Ulna
114 . . . Tendon

The invention claimed is:

1. A sensor module, comprising:
a sensor base;
a pressure sensor portion fixed to the sensor base;
a sensor head cover including,
on an outer surface, an opening in a region that comes into contact with a living body and
an inner surface formed with unevenness,
the sensor head cover being fixed to the sensor base and forming a gap portion that communicates with the opening between the inner surface, the sensor base, and the pressure sensor portion; and
a soft portion disposed in the gap portion and, at least, filling up the opening and covering the pressure sensor portion, the soft portion allowing pressure of the living body to transfer to the pressure sensor portion, wherein
the unevenness of the inner surface is formed by roughening surface roughness;
the region of the outer surface of the sensor head cover that comes into contact with the living body includes a flat surface portion formed as a flat surface with surface roughness less than the surface roughness of the inner surface; and
the opening is formed in the flat surface portion.

2. The sensor module according to claim 1, wherein the inner surface is formed with leather-like grains.

3. The sensor module according to claim 1, wherein the flat surface portion is provided with mirror surface processing.

4. The sensor module according to claim 3, wherein the sensor head cover is formed from ceramic.

5. The sensor module according to claim 1, wherein
an entire region of the region of the outer surface of the sensor head cover that comes into contact with the living body has identical surface roughness.

6. The sensor module according to claim 1, wherein the sensor head cover is formed from ceramic.

7. A method for manufacturing a sensor module, comprising:
fixing a pressure sensor portion to one main surface of a sensor base that includes a support wall portion in which a flow hole is formed extending through from the one main surface to another main surface;
fixing a sensor head cover including:
an opening in a flat surface portion of a region on an outer surface that comes into contact with a living body and
an inner surface formed with unevenness
to the sensor base and forming a gap portion that communicates with the flow hole between the inner surface, the sensor base, and the pressure sensor portion;
closing off the opening with an opposing member by bringing the opposing member into contact with the flat surface portion;
injecting a material for forming a soft portion into the flow hole from the other main surface; and
separating the opposing member from the sensor head cover after the soft portion is formed from the material.

8. A blood pressure measurement device, comprising:
a sensor module including:
a sensor base;
a pressure sensor portion fixed to the sensor base;
a sensor head cover including,
on an outer surface, an opening in a region that comes into contact with a living body and
an inner surface formed with unevenness,
the sensor head cover being fixed to the sensor base and forming a gap portion that communicates with the opening between the inner surface, the sensor base, and the pressure sensor portion; and
a soft portion disposed in the gap portion and, at least, filling up the opening and covering the pressure sensor portion, the soft portion allowing pressure of the living body to transfer to the pressure sensor portion;
an attach portion including:
an opening portion provided at a position opposite the living body, the sensor module being disposed in the opening portion, and
an end surface that curves conforming to a shape in a circumferential direction of a portion of the living body;
a fastener provided on the attach portion; and
a case provided on the attach portion, the case housing the sensor module, wherein
the unevenness of the inner surface is formed by roughening surface roughness;
the region of the outer surface of the sensor head cover that comes into contact with the living body includes a flat surface portion formed as a flat surface with surface roughness less than the surface roughness of the inner surface; and
the opening is formed in the flat surface portion.

* * * * *